United States Patent
Jackson

(10) Patent No.: US 11,950,809 B2
(45) Date of Patent: Apr. 9, 2024

(54) DYNAMIC STABILIZATION WITH RELEASABLE END BLOCKER-BUMPER

(71) Applicant: Roger P. Jackson, Prairie Village, KS (US)

(72) Inventor: Roger P. Jackson, Prairie Village, KS (US)

(*) Notice: Subject to any disclaimer, the term of this patent is extended or adjusted under 35 U.S.C. 154(b) by 115 days.

(21) Appl. No.: 17/236,792

(22) Filed: Apr. 21, 2021

(65) Prior Publication Data

US 2021/0251666 A1    Aug. 19, 2021

Related U.S. Application Data

(63) Continuation of application No. 16/195,086, filed on Nov. 19, 2018, now Pat. No. 11,006,979, which is a continuation of application No. 15/237,173, filed on Aug. 15, 2016, now Pat. No. 10,130,393, which is a continuation of application No. 13/199,772, filed on Sep. 8, 2011, now Pat. No. 9,451,989, and a continuation-in-part of application No. 12/802,849, filed on Jun. 15, 2010, now abandoned.

(60) Provisional application No. 61/402,942, filed on Sep. 8, 2010, provisional application No. 61/396,390, filed on May 26, 2010, provisional application No. 61/395,752, filed on May 17, 2010, provisional application No. 61/395,564, filed on May 14, 2010, provisional application No. 61/336,911, filed on Jan. 28, 2010, provisional application No. 61/270,754, filed on Jul. 13, 2009, provisional application No. 61/268,708, filed on Jun. 15, 2009.

(51) Int. Cl.
*A61B 17/70* (2006.01)
*A61B 17/00* (2006.01)

(52) U.S. Cl.
CPC ...... *A61B 17/7022* (2013.01); *A61B 17/7005* (2013.01); *A61B 17/7008* (2013.01); *A61B 17/702* (2013.01); *A61B 17/7029* (2013.01); *A61B 17/7031* (2013.01); *A61B 17/7032* (2013.01); *A61B 17/7053* (2013.01); *A61B 2017/00862* (2013.01); *A61B 2017/00964* (2013.01); *A61B 17/7037* (2013.01)

(58) Field of Classification Search
CPC .............. A61B 17/702; A61B 17/7022; A61B 17/7026; A61B 17/7031; A61B 17/7014; A61B 17/7005; A61B 17/7032
See application file for complete search history.

(56) References Cited

U.S. PATENT DOCUMENTS

| | | |
|---|---|---|
| 5,171,279 A | 12/1992 | Mathews |
| D346,217 S | 4/1994 | Sparker et al. |
| 5,569,253 A | 10/1996 | Farris et al. |

(Continued)

*Primary Examiner* — Julianna N Harvey
(74) *Attorney, Agent, or Firm* — Polsinelli PC

(57) ABSTRACT

A medical implant assembly having at least two bone attachment structures cooperating with a dynamic longitudinal connecting member, the improvement wherein the connecting member includes: a first end, a transition portion, and a second end; a substantially rod portion extending longitudinally from the first end to the transition portion, and including a longitudinal axis and a substantially rigid core running substantially parallel with the longitudinal axis; a substantially cord portion joined with the rod portion and extending from the transition portion to the second end; and a substantially flexible jacket portion covering the rod and cord portions.

17 Claims, 8 Drawing Sheets

(56) References Cited

U.S. PATENT DOCUMENTS

| | | | |
|---|---|---|---|
| 6,132,431 A | 10/2000 | Nilsson et al. | |
| 6,248,106 B1 | 6/2001 | Ferree | |
| 6,251,112 B1 | 6/2001 | Jackson | |
| 6,280,442 B1 | 8/2001 | Barker | |
| 6,290,700 B1 | 9/2001 | Schmotzer | |
| 6,565,565 B1 | 5/2003 | Yuan et al. | |
| 6,997,927 B2 | 2/2006 | Jackson | |
| 7,713,288 B2 | 5/2010 | Timm et al. | |
| 7,815,665 B2 | 10/2010 | Jahng et al. | |
| 7,828,825 B2 | 11/2010 | Bruneau et al. | |
| 7,842,072 B2 | 11/2010 | Dawson | |
| 7,901,437 B2 | 3/2011 | Jackson | |
| 7,988,710 B2 | 8/2011 | Jahng et al. | |
| 8,029,544 B2 | 10/2011 | Hested et al. | |
| 8,114,133 B2 | 2/2012 | Logan | |
| 8,128,667 B2 | 3/2012 | Jackson | |
| 8,157,843 B2 | 4/2012 | Biederman et al. | |
| 8,292,926 B2 | 10/2012 | Jackson | |
| 8,366,745 B2 | 2/2013 | Jackson | |
| 8,465,526 B2 | 6/2013 | Friedrich et al. | |
| 9,101,404 B2 | 8/2015 | Jackson | |
| 9,439,683 B2 | 9/2016 | Jackson | |
| 9,451,989 B2 | 9/2016 | Jackson | |
| 9,668,771 B2 | 6/2017 | Jackson | |
| 9,750,540 B2 | 9/2017 | Jackson | |
| 9,861,394 B2 | 1/2018 | Jackson | |
| 9,931,139 B2 | 4/2018 | Jackson | |
| 9,956,002 B2 | 5/2018 | Jackson | |
| 10,130,393 B2 | 11/2018 | Jackson | |
| 10,206,716 B2 | 2/2019 | Jackson et al. | |
| 10,258,382 B2 | 4/2019 | Jackson | |
| 10,383,660 B2 | 8/2019 | Jackson | |
| 10,470,801 B2 | 11/2019 | Jackson | |
| 10,617,447 B2 | 4/2020 | Jackson | |
| 10,729,469 B2 | 8/2020 | Jackson | |
| 2002/0035366 A1 | 3/2002 | Walder et al. | |
| 2002/0055740 A1 | 5/2002 | Lieberman | |
| 2002/0107570 A1 | 8/2002 | Sybert et al. | |
| 2002/0116001 A1 | 8/2002 | Schafer | |
| 2002/0116065 A1 | 8/2002 | Jackson | |
| 2002/0198526 A1 | 12/2002 | Shaolian et al. | |
| 2003/0083657 A1 | 5/2003 | Drewry et al. | |
| 2003/0212398 A1 | 11/2003 | Jackson | |
| 2004/0049190 A1 | 3/2004 | Biederman et al. | |
| 2004/0138662 A1 | 7/2004 | Landry et al. | |
| 2004/0143265 A1 | 7/2004 | Landry et al. | |
| 2004/0167523 A1 | 8/2004 | Jackson | |
| 2004/0172032 A1 | 9/2004 | Jackson | |
| 2004/0215191 A1 | 10/2004 | Kitchen | |
| 2004/0236327 A1 | 11/2004 | Paul et al. | |
| 2004/0236328 A1 | 11/2004 | Paul et al. | |
| 2005/0010220 A1 | 1/2005 | Casutt et al. | |
| 2005/0085815 A1 | 4/2005 | Harms et al. | |
| 2005/0131407 A1 | 6/2005 | Sicvol et al. | |
| 2005/0149020 A1 | 7/2005 | Jahng | |
| 2005/0203514 A1* | 9/2005 | Jahng | A61B 17/1757 606/907 |
| 2005/0203517 A1* | 9/2005 | Jahng | A61B 17/7007 606/907 |
| 2005/0277919 A1 | 12/2005 | Slivka et al. | |
| 2005/0277920 A1 | 12/2005 | Slivka et al. | |
| 2005/0277922 A1 | 12/2005 | Trieu et al. | |
| 2005/0277932 A1 | 12/2005 | Farris | |
| 2005/0288671 A1 | 12/2005 | Yuan et al. | |
| 2005/0288672 A1 | 12/2005 | Ferree | |
| 2006/0025767 A1 | 2/2006 | Khalili | |
| 2006/0036240 A1 | 2/2006 | Colleran et al. | |
| 2006/0058788 A1 | 3/2006 | Hammer et al. | |
| 2006/0064090 A1 | 3/2006 | Park | |
| 2006/0079894 A1 | 4/2006 | Colleran et al. | |
| 2006/0142760 A1 | 6/2006 | McDonnell | |
| 2006/0149238 A1 | 7/2006 | Sherman et al. | |
| 2006/0241602 A1 | 10/2006 | Jackson | |
| 2006/0241769 A1 | 10/2006 | Gordon et al. | |
| 2006/0247635 A1 | 11/2006 | Gordon et al. | |
| 2006/0247779 A1 | 11/2006 | Gordon et al. | |
| 2006/0264937 A1 | 11/2006 | White | |
| 2007/0005063 A1 | 1/2007 | Bruneau et al. | |
| 2007/0032123 A1 | 2/2007 | Timm et al. | |
| 2007/0100341 A1 | 5/2007 | Reglos et al. | |
| 2007/0118123 A1 | 5/2007 | Strausbaugh et al. | |
| 2007/0123864 A1 | 5/2007 | Walder et al. | |
| 2007/0129729 A1 | 6/2007 | Petit et al. | |
| 2007/0191841 A1 | 8/2007 | Justis et al. | |
| 2007/0233064 A1 | 10/2007 | Holt | |
| 2007/0233075 A1 | 10/2007 | Dawson | |
| 2007/0270821 A1* | 11/2007 | Trieu | A61B 17/7031 606/279 |
| 2007/0270840 A1 | 11/2007 | Chin et al. | |
| 2007/0276380 A1 | 11/2007 | Jahng et al. | |
| 2007/0288011 A1 | 12/2007 | Logan | |
| 2008/0021469 A1 | 1/2008 | Holt | |
| 2008/0051787 A1 | 2/2008 | Remington et al. | |
| 2008/0086125 A1 | 4/2008 | Molz et al. | |
| 2008/0086130 A1 | 4/2008 | Lake | |
| 2008/0091214 A1* | 4/2008 | Richelsoph | A61B 17/7029 606/103 |
| 2008/0161857 A1 | 7/2008 | Hestad et al. | |
| 2008/0183213 A1 | 7/2008 | Veldman et al. | |
| 2008/0234691 A1 | 9/2008 | Schwab | |
| 2008/0234737 A1 | 9/2008 | Boschert | |
| 2008/0234744 A1* | 9/2008 | Zylber | A61B 17/7022 606/264 |
| 2008/0262551 A1 | 10/2008 | Rice et al. | |
| 2008/0262553 A1 | 10/2008 | Hawkins et al. | |
| 2008/0275504 A1 | 11/2008 | Bonin et al. | |
| 2008/0294198 A1 | 11/2008 | Jackson | |
| 2008/0319482 A1 | 12/2008 | Jackson | |
| 2008/0319486 A1 | 12/2008 | Hestad et al. | |
| 2009/0005817 A1 | 1/2009 | Friedrich et al. | |
| 2009/0012562 A1* | 1/2009 | Hestad | A61B 17/7031 606/246 |
| 2009/0036924 A1 | 2/2009 | Egli et al. | |
| 2009/0054932 A1 | 2/2009 | Butler et al. | |
| 2009/0082815 A1 | 3/2009 | Zylber et al. | |
| 2009/0088799 A1 | 4/2009 | Yeh | |
| 2009/0093846 A1 | 4/2009 | Hestad | |
| 2009/0099606 A1 | 4/2009 | Hestad et al. | |
| 2009/0105757 A1 | 4/2009 | Gimbel et al. | |
| 2009/0105758 A1 | 4/2009 | Gimbel et al. | |
| 2009/0177231 A1 | 7/2009 | Kiester | |
| 2009/0198280 A1 | 8/2009 | Spratt et al. | |
| 2009/0204152 A1 | 8/2009 | Blain | |
| 2009/0228045 A1 | 9/2009 | Hayes et al. | |
| 2009/0240285 A1 | 9/2009 | Friedrich et al. | |
| 2009/0240286 A1 | 9/2009 | Friedrich et al. | |
| 2009/0259257 A1 | 10/2009 | Prevost | |
| 2009/0275983 A1 | 11/2009 | Veldman et al. | |
| 2009/0299411 A1 | 12/2009 | Laskowitz et al. | |
| 2010/0010542 A1 | 1/2010 | Jackson | |
| 2010/0010543 A1 | 1/2010 | Jackson | |
| 2010/0036423 A1 | 2/2010 | Hayes | |
| 2010/0137912 A1 | 6/2010 | Alcock et al. | |
| 2010/0174319 A1 | 7/2010 | Jackson | |
| 2010/0211105 A1 | 8/2010 | Moumene et al. | |
| 2010/0228292 A1 | 9/2010 | Arnold et al. | |
| 2010/0331887 A1 | 12/2010 | Jackson et al. | |
| 2011/0004222 A1 | 1/2011 | Biedermann et al. | |
| 2011/0301644 A1 | 12/2011 | Belliard | |
| 2012/0035660 A1 | 2/2012 | Jackson | |
| 2012/0053636 A1 | 3/2012 | Schmocker | |
| 2012/0221054 A1 | 8/2012 | Jackson | |
| 2013/0123853 A1 | 5/2013 | Seme et al. | |
| 2013/0197582 A1 | 8/2013 | Prevost et al. | |
| 2014/0039555 A1 | 2/2014 | Jackson | |
| 2014/0222076 A1 | 8/2014 | Jackson | |
| 2014/0343610 A1 | 11/2014 | Jackson | |
| 2014/0379030 A1 | 12/2014 | Jackson | |
| 2015/0216567 A1 | 8/2015 | Trautwein et al. | |
| 2015/0230827 A1 | 8/2015 | Zylber et al. | |
| 2015/0320449 A1 | 11/2015 | Jackson | |
| 2016/0310169 A1 | 10/2016 | Jackson et al. | |
| 2016/0354118 A1 | 12/2016 | Belliard et al. | |
| 2017/0100165 A1 | 4/2017 | Jackson | |

(56) References Cited

U.S. PATENT DOCUMENTS

| | | |
|---|---|---|
| 2017/0231662 A1 | 8/2017 | Jackson |
| 2018/0168693 A1 | 6/2018 | Jackson et al. |
| 2018/0185068 A1 | 7/2018 | Jackson |
| 2018/0221063 A1 | 8/2018 | Jackson |
| 2019/0231395 A1 | 8/2019 | Jackson |
| 2019/0239925 A1 | 8/2019 | Jackson |
| 2019/0365427 A1 | 8/2019 | Jackson |
| 2020/0138482 A1 | 5/2020 | Jackson |

* cited by examiner

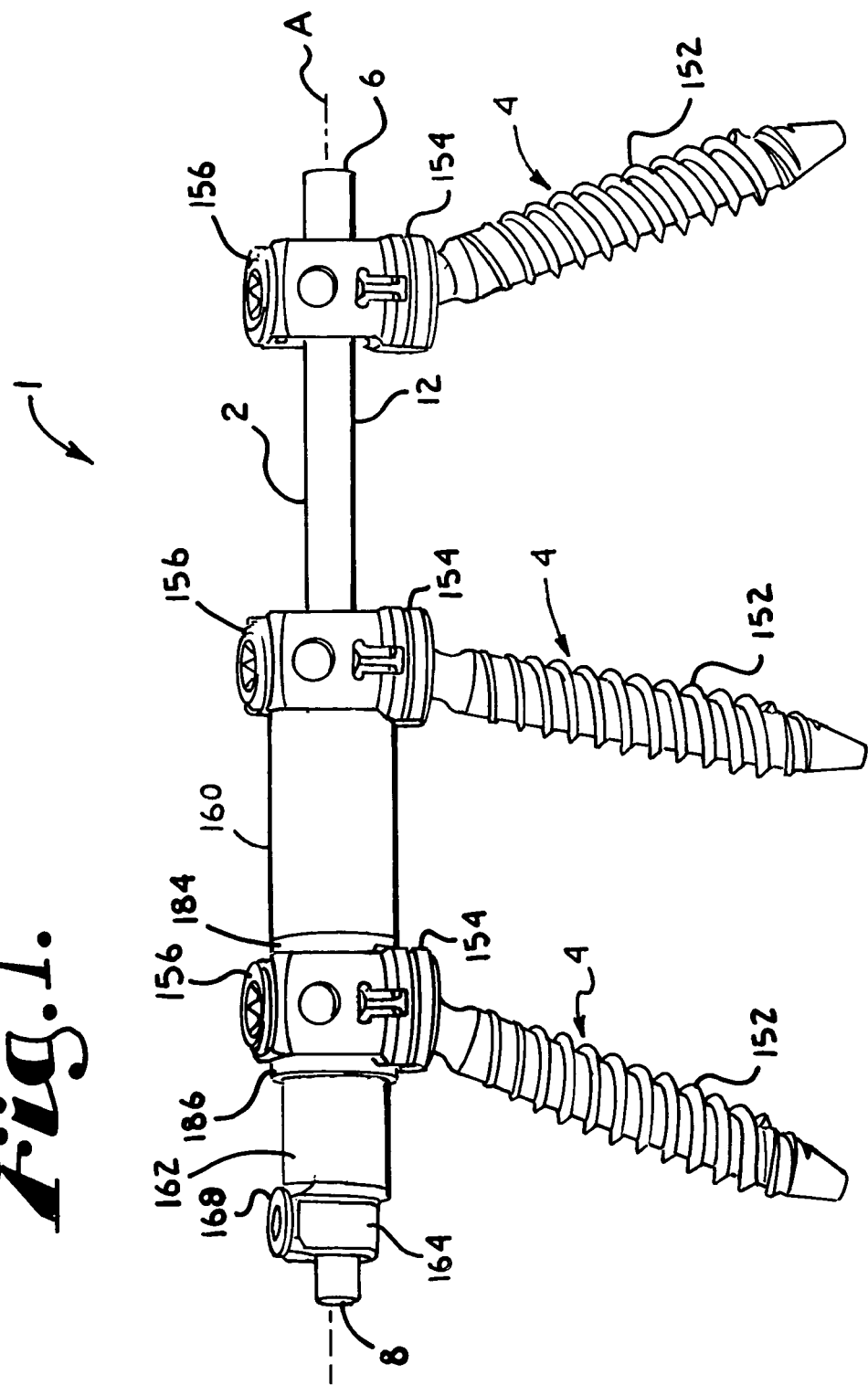

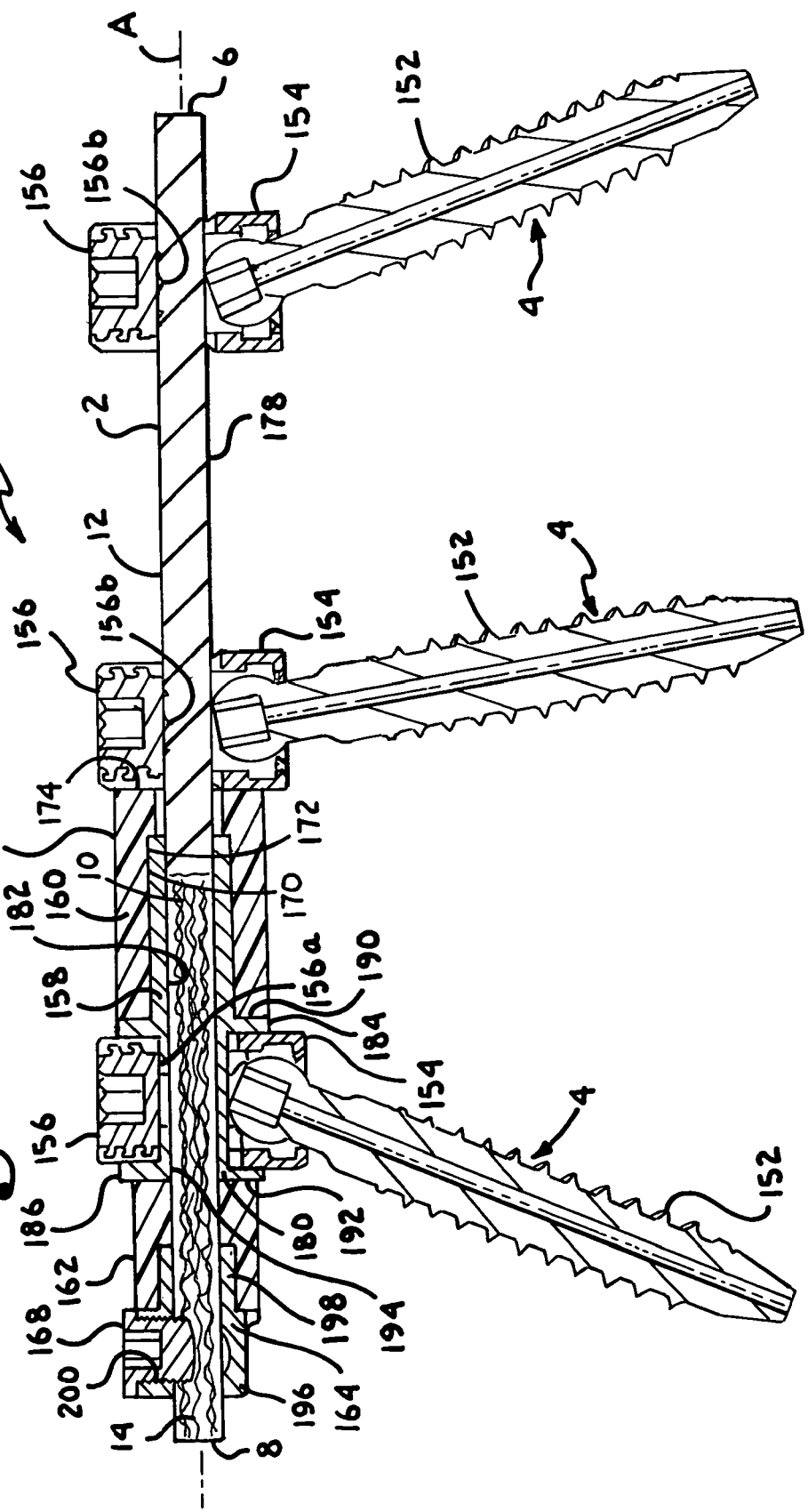

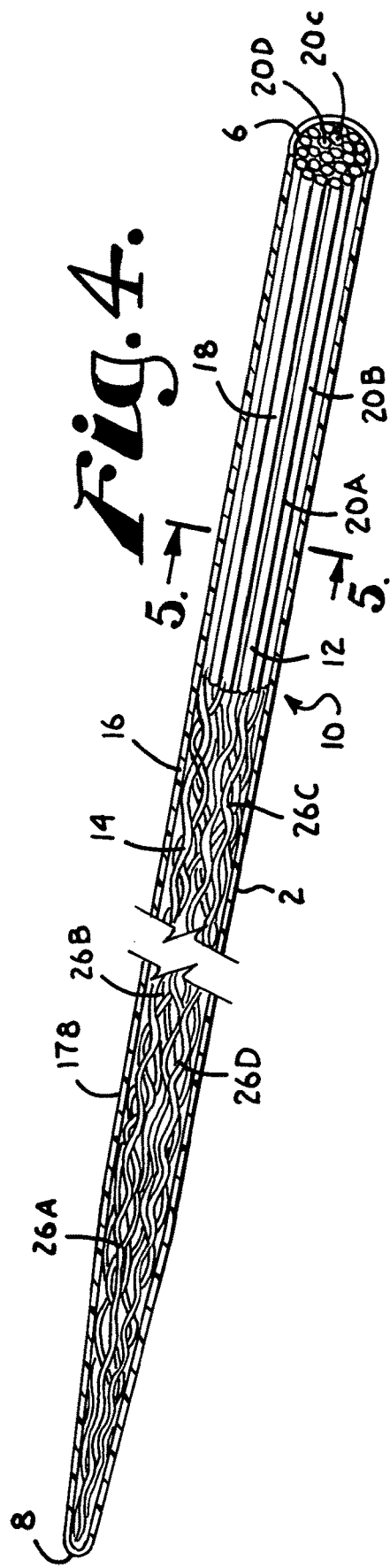
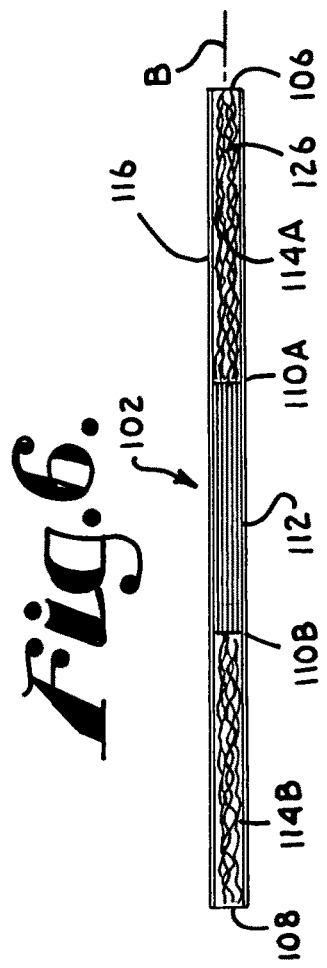
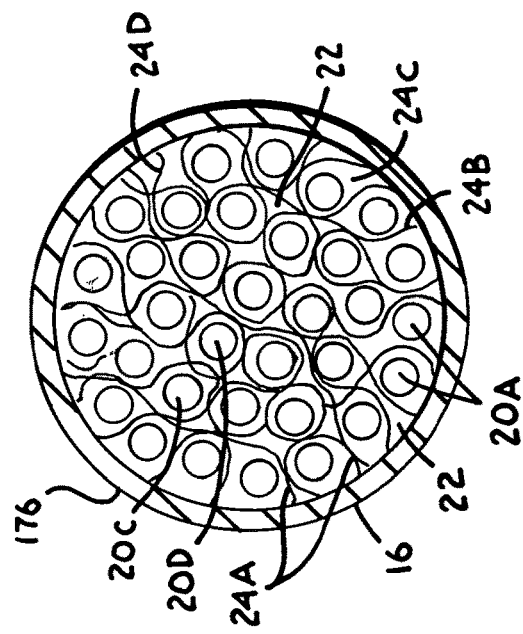

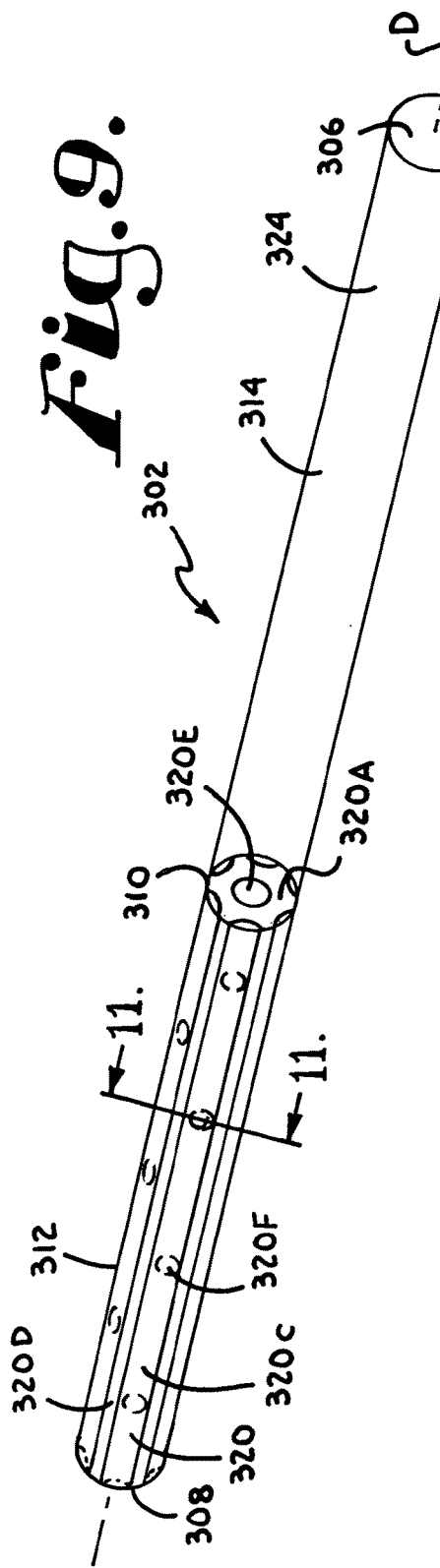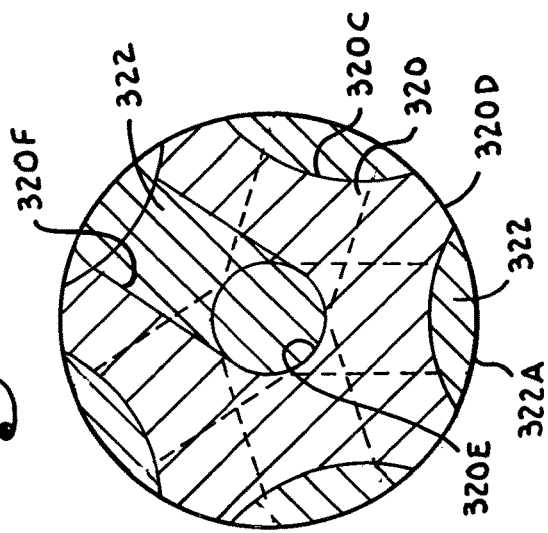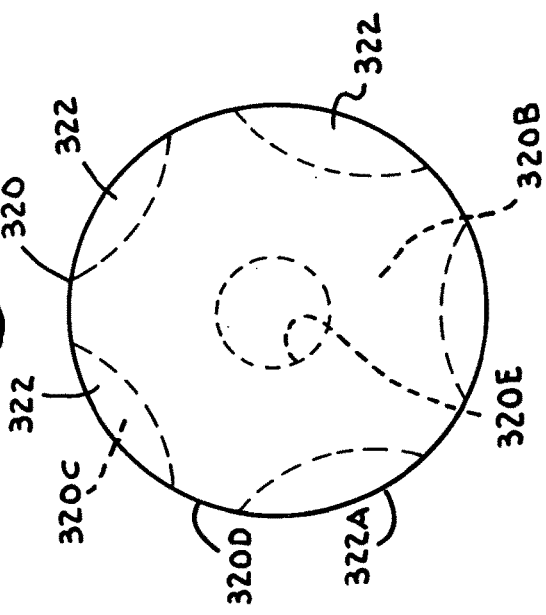

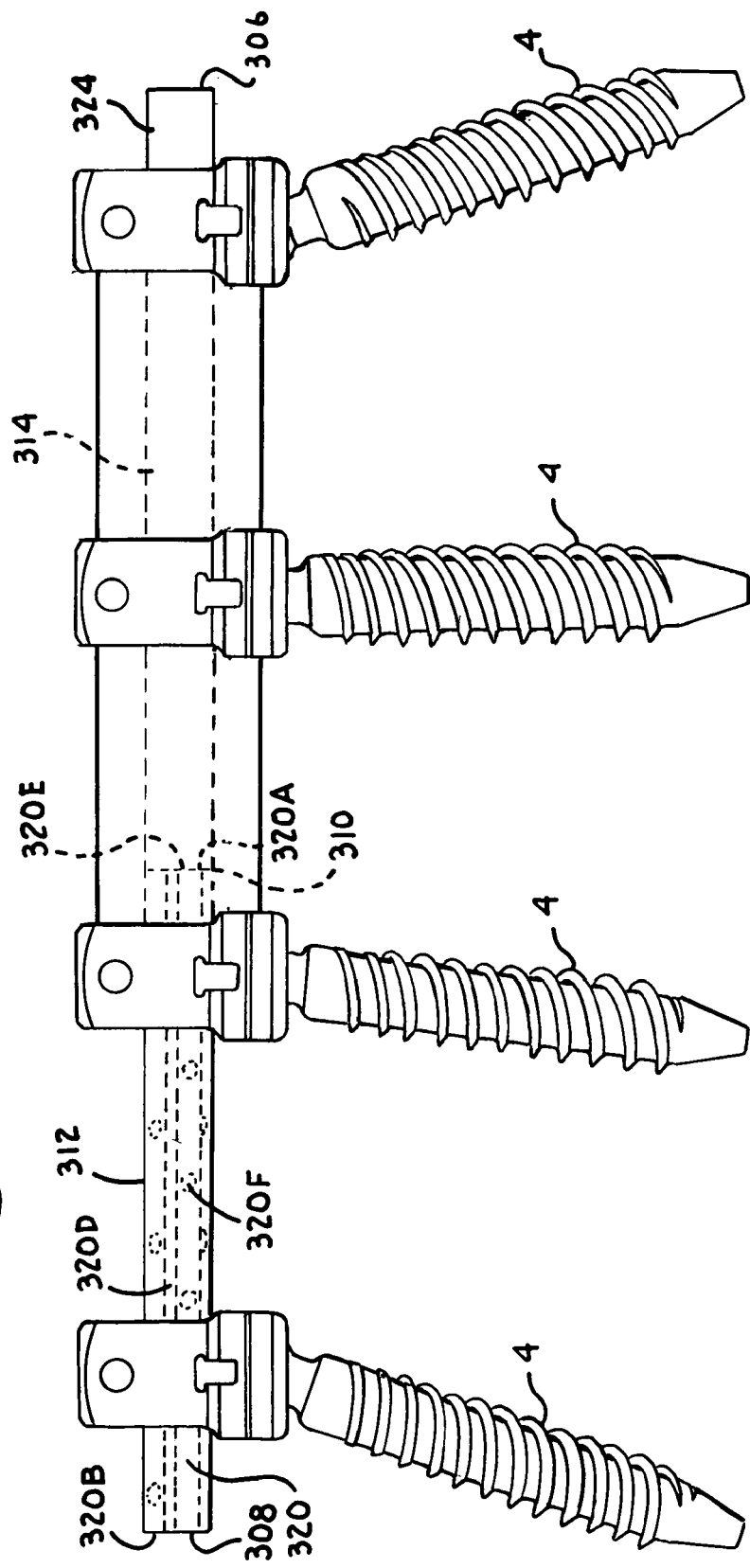

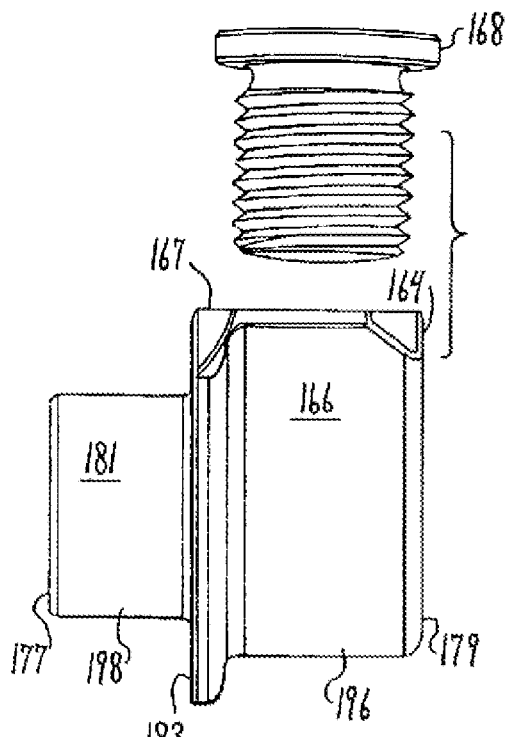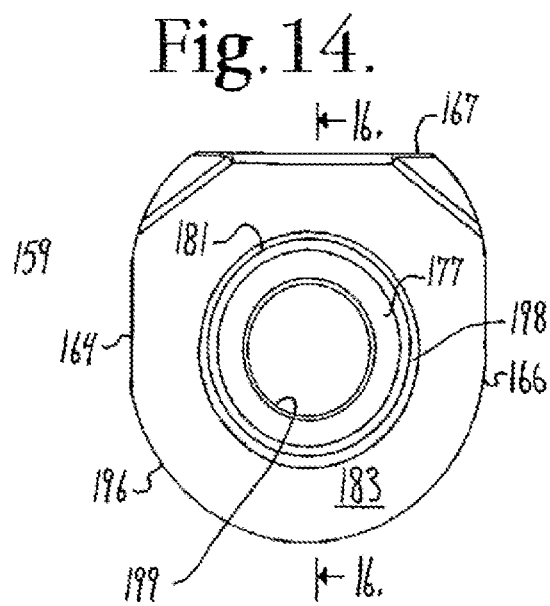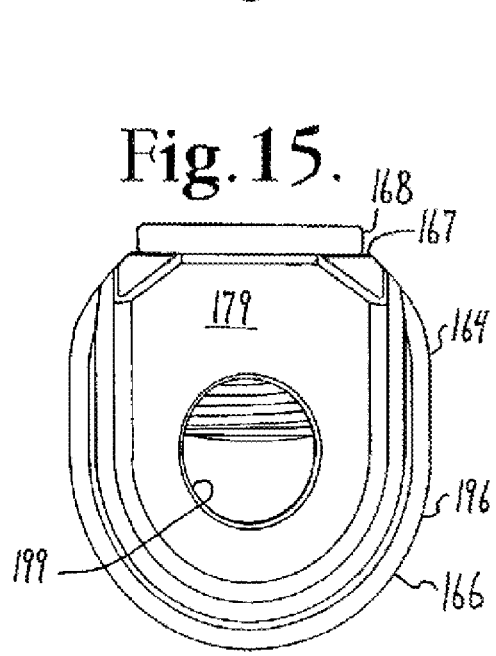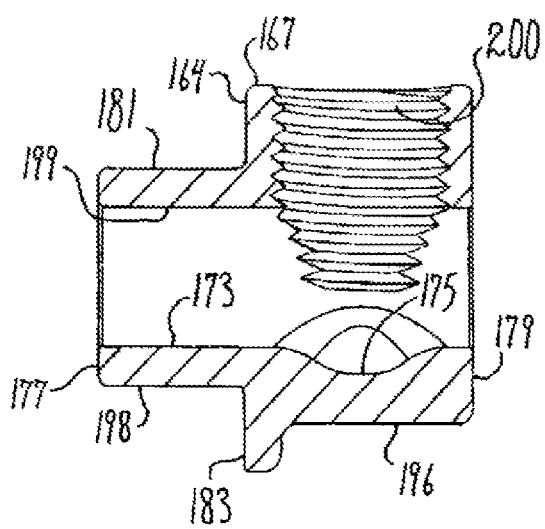

DYNAMIC STABILIZATION WITH RELEASABLE END BLOCKER-BUMPER

CROSS-REFERENCE TO RELATED APPLICATIONS

This application is a continuation of U.S. application Ser. No. 16/195,086 filed Nov. 19, 2018, which is a continuation of U.S. application Ser. No. 15/237,173, filed Aug. 15, 2016, now U.S. Pat. No. 10,130,393, which is a continuation of U.S. application Ser. No. 13/199,772, filed Sep. 8, 2011, now U.S. Pat. No. 9,451,989, which claims the benefit of U.S. Provisional Application No. 61/402,942, filed Sep. 8, 2010, and is a continuation-in-part of U.S. application Ser. No. 12/802,849, filed Jun. 15, 2010, which claims the benefits of U.S. Provisional Application No. 61/268,708, filed Jun. 15, 2009, U.S. Provisional Application No. 61/270,754, filed Jul. 13, 2009, U.S. Provisional Application No. 61/336,911, filed Jan. 28, 2010, U.S. Provisional Application No. 61/395,564, filed May 14, 2010, U.S. Provisional Application No. 61/395,752, filed May 17, 2010, and U.S. Provisional Application No. 61/396,390, filed May 26, 2010. All of the aforementioned applications are hereby incorporated by reference in theft entireties into the present application for any and ail purposes.

BACKGROUND OF THE INVENTION

The present invention is directed to dynamic fixation assemblies for use in bone surgery, particularly spinal surgery, and in particular to longitudinal connecting members for such assemblies, the connecting members being attached to at least two bone fasteners.

Historically, it has been common to fuse adjacent vertebrae that are placed in fixed relation by the installation therealong of bone screws or other bone attachment members, or bone anchors, and cooperating longitudinal connecting members or other elongate members. Fusion results in the permanent immobilization of one or more of the intervertebral joints. Because the anchoring of bone screws, hooks and other types of anchors directly to a vertebra can result in significant forces being placed on the vertebra, and such forces may ultimately result in the loosening of the bone screw or other anchor from the vertebra, fusion allows for the growth and development of a bone counterpart to the longitudinal connecting member that can maintain the spine in the desired position even if the implants ultimately fail or are removed. Because fusion has been a desired component of spinal stabilization procedures, longitudinal connecting members have been designed that are of a material, size and shape to largely resist flexure, extension, torsion, distraction and compression, and thus substantially immobilize the portion of the spine that is to be fused. Thus, longitudinal connecting members are typically uniform along an entire length thereof, and usually made from a single or integral piece of material having a uniform diameter or width of a size to provide substantially rigid support in all planes.

Fusion, however, has some undesirable side effects. One apparent side effect is the immobilization of a portion of the spine. Furthermore, although fusion may result in a strengthened portion of the spine, it also has been linked to more rapid degeneration due to increased stresses and even hypermobility and collapse of spinal motion segments that are adjacent to the portion of the spine being fused, reducing or eliminating the ability of such spinal joints to move in a more normal relation to one another. In certain instances, fusion has also failed to provide pain relief.

An alternative to fusion and the use of more rigid longitudinal connecting members or other rigid structure has been a "soft" or "dynamic" stabilization approach in which a flexible loop-, S-, C- or U-shaped member or a coil-like and/or a spring-like member is utilized as an elastic longitudinal connecting member fixed between a pair of pedicle screws in an attempt to create, as much as possible, a normal loading pattern between the vertebrae in flexion, extension, distraction, compression, side bending and torsion. Problems may arise with such devices, however, including tissue scarring, lack of adequate spinal support and lack of fatigue strength or endurance limit. Fatigue strength has been defined as the repeated loading and unloading of a specific stress on a material structure until it fails. Fatigue strength can be tensile or distraction, compression, shear, torsion, bending, or a combination of these.

Another type of soft or dynamic system known in the art includes bone anchors connected by flexible cords or strands, typically made from a plastic material. Such a cord or strand may be threaded through cannulated spacers that are disposed between and in contact with adjacent bone anchors when such a cord or strand is implanted, tensioned and attached to or compressed against the bone anchors. The spacers typically span the distance between the bone anchors, providing limits on the bending movement of the cord or strand and thus strengthening and supporting the overall system. Such cord or strand-type systems typically require specialized bone anchors and tooling for tensioning and holding the chord or strand in the bone anchors. Thus a major disadvantage of such cord and spacer systems is their lack of interchangeability with more rigid rod systems, especially those systems that incorporate polyaxial screws as bone anchors.

The complex dynamic conditions associated with spinal movement therefore provide quite a challenge for the design of more flexible and/or elastic elongate longitudinal connecting members that exhibit an adequate fatigue strength to provide stabilization and protected motion of the spine, without fusion, and allow for some natural movement of the portion of the spine being reinforced and supported by the elongate elastic or flexible connecting member. A further challenge are situations in which a portion or length of the spine requires a more rigid stabilization, possibly including fusion with deformity correction, while another portion or length may be better supported by a more dynamic component that allows for protected movement or stress relief, especially adjacent to a long rigid rod construct. In such cases a more rigid longitudinal connecting member can be attached to a cord member of varying length.

SUMMARY OF THE INVENTION

An improved dynamic longitudinal connecting member according to the invention, for use in a medical implant assembly having at least two bone attachment members cooperating with the dynamic longitudinal connecting member, is provided. The improved connecting member includes a first end, a transition portion and a second end. A substantially rigid rod portion extends longitudinally from the first end to the transition portion, and includes a longitudinal axis and a substantially rigid core running substantially parallel with the longitudinal axis. A substantially flexible cord portion is joined with the rigid rod portion and extends from the transition portion to the second end. A substantially flexible jacket portion covers the rod and cord portions.

In a further embodiment, the rod portion includes a plurality of substantially rigid longitudinally extending rodlets. In some embodiments, the rod portion includes a binding material adapted for joining the rodlets together. In some embodiments, the rod portion includes a plurality of filamentous structures. In some further embodiments, the filamentous structures at least partially surround the rodlets. In some further embodiments, the filamentous structures are substantially flexible. In some further embodiments, the filamentous structures include at least one polymer.

In a further embodiment, the cord portion is in tension.

In a further embodiment, the cord portion includes a plurality of substantially flexible strands extending from about the transition portion towards the second end. In some embodiments, the strands are braided. In some embodiments, the strands are coiled. In some embodiments, the strands are random. In some embodiments, the strands are embedded in an elastomer. In some embodiments, the strands include a polymer. In some embodiments, the strands include a mixture of a polymer and a plurality of at least one of fibers and filaments.

In a further embodiment, the cord portion is a substantially elastic polymer filament.

In a further embodiment, the cord portion is a polymer rod. In some embodiments, the polymer rod includes a substantially elastic polymer. In some embodiments, the polymer rod includes a composite of at least two polymers.

In a further embodiment, the cord portion includes a flexible cable.

In a further embodiment, the cord portion includes a flexible cord.

In a further embodiment, a spacer covers the transition portion. In some embodiments, the spacer extends between the at least two bone attachment members. In some embodiments, the spacer is substantially elastic.

In a further embodiment, a sleeve is located between the cord portion and one of the at least two bone attachment members. In some embodiments, the sleeve includes a through-bore in sliding engagement with the cord portion.

In a further embodiment, the rod portion is an inelastic stent structure at least partially embedded in an elastomer. In some embodiments, the rod portion includes a substantially cylindrical outer surface; and the stent structure includes a longitudinally extending lumen and a plurality of longitudinally oriented concave grooves adapted for contacting the elastomer. In some embodiments, the stent structure includes a plurality of bores extending radially from the lumen to one of the plurality of concave grooves. In some embodiments, the cord portion includes a substantially flexible rod formed of the elastomer; and wherein the elastomer fills the lumen and the bores.

In a further embodiment, the assembly includes an elastic bumper and a cord blocker.

BRIEF DESCRIPTION OF THE DRAWINGS

The drawings constitute a part of this specification and include exemplary embodiments of the present invention and illustrate various objects and features thereof.

FIG. 1 is a front elevational view of a dynamic fixation longitudinal connecting member assembly according to the invention showing a dynamic fixation longitudinal connecting member according to the invention shown attached to three polyaxial bone screws of the invention.

FIG. 3 is an enlarge cross-sectional view of the assembly of FIG. 1, taken on line 3-3 of FIG. 1 *a*.

FIG. 4 is front elevational view of the dynamic fixation longitudinal connecting member of FIG. 1, with portions broken away to show detail thereof, including a rod portion and a cord portion.

FIG. 5 is an enlarged cross-sectional view of the dynamic fixation longitudinal connecting member of FIG. 4, taken along the line 5-5 of FIG. 4.

FIG. 6 is front elevational view of a second embodiment of a dynamic fixation longitudinal connecting member according to the invention, with portions broken away to show detail thereof, including two cord portions joined by a rod portion.

FIG. 9 is a perspective view of a fourth embodiment of a dynamic fixation longitudinal connecting member according to the invention, including a rigid first rod portion and an elastic second rod portion.

FIG. 10 is an enlarged left side view of the dynamic fixation longitudinal connecting member of FIG. 9.

FIG. 11 is an enlarged cross-sectional view of the dynamic fixation longitudinal connecting member of FIG. 9, taken along the line 11-11 of FIG. 9.

FIG. 12 is a front elevational view of the dynamic fixation longitudinal connecting member of FIG. 9, shown with four bone attachment members and two spacers according to the invention, with portions shown in phantom to show detail thereof.

FIG. 13 is an enlarged side elevational view of the blocker and set screw shown in FIG. 1.

FIG. 14 is an enlarged rear elevational view of the blocker of FIG. 13.

FIG. 15 is an enlarged front elevational view of the blocker and set screw of FIG. 13.

FIG. 16 is an enlarged cross-sectional view taken along the line 16-16 of FIG. 14.

DETAILED DESCRIPTION OF THE INVENTION

Figure 1A:
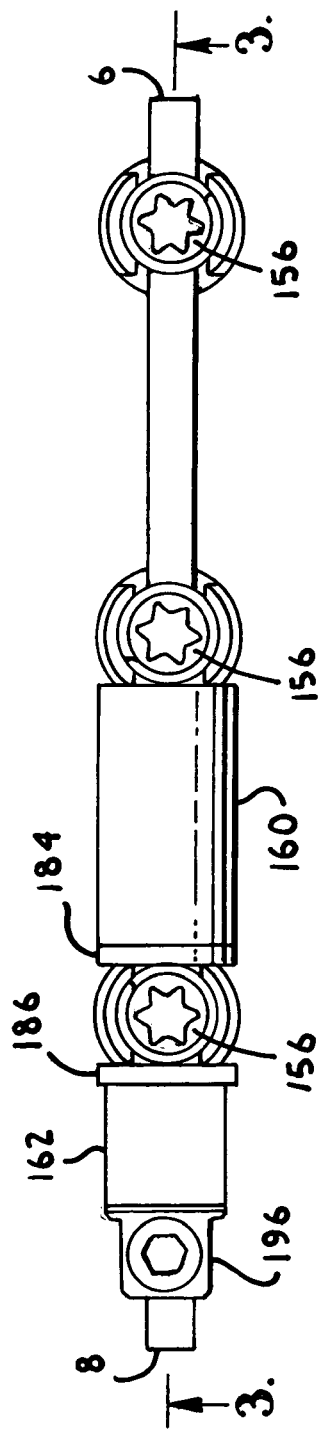
FIG. 1*a* is a top view of the assembly of FIG. 1.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment members in actual use.

With reference to FIGS. 1-5 the reference number 1 generally designates a non-fusion dynamic stabilization longitudinal connecting member assembly according to the present invention. The connecting member assembly 1 generally includes a dynamic longitudinal connecting member 2 in cooperation with at least two bone attachment members 4, such as bone screws, anchors or hooks, as described below with reference to FIG. 1. The longitudinal axis of the assembly 1 is denoted by the letter A.

The connecting member 2 extends longitudinally from a first end 6 to a second end 8 thereof, with a transition portion 10 located therebetween. The connecting member 2 is substantially cylindrical, with a substantially circular cross-section. The diameter of the connecting member 2 is sized for engagement by the bone attachment members 4 and is substantially uniform, constant or unchanging, along its length, with optional exceptions discussed below. It is foreseen that the connecting member 2 may have other forms, including but not limited to oval, square and rectangular cross-sections as well as other curved or polygonal shapes.

The connecting member 2 includes rod and cord portions 12 and 14. The rod and cord portions 12 and 14 have differing relative level of rigidity, flexibility or deformability, depending upon the support requirements of the implant assembly 1. Generally, the rod portion 12 is more rigid and less deformable than the cord portion 14. A flexible jacket portion 16 covers the connecting member 2, providing a substantially smooth, strong and resilient outer surface thereto.

Referring to FIGS. 4-5, the rod portion 12 is a substantially rigid rod-shaped structure extending longitudinally from the first end 6 to the transition portion 10. The rod portion 12 is of a length for cooperating with at least one and up to a plurality of bone attachment members 4, such as bone screws or hooks, and may be cut to the desired length during implantation. For example, in FIGS. 1 and 3, the rod portion 12 is shown cooperatively engaged by two bone anchors 4. The rod portion 12 has a substantially circular cross-section along its length, with a diameter sufficient for engagement by the bone anchor(s) 4. Generally, the diameter of the rod portion 12 is substantially uniform, or constant, along the length thereof. It is foreseen, however, that the rod portion 12 may have other forms, including but not limited to oval, square and rectangular cross-sections as well as other curved or polygonal shapes.

The rod portion 12 includes a substantially rigid core 16 that runs substantially parallel with the longitudinal axis A, from the first end 6 to the transition portion 10. The core 16 includes a plurality of very thin, long, cylindrical rodlets, some of which are denoted by the numerals 20 *a*, 20 *b*, 20 *c* and 20 *d*.

The longitudinally extending rodlets 20 *a*, 20 *b*, 20 *c* and 20 *d* are bundled or grouped together. A sufficient number of the rodlets 20 *a*, 20 *b*, 20 *c* and 20 *d* is included in the bundle so as to render the rod portion 12, as a whole, substantially rigid or non-elastic. Generally, the individual rodlets 20 *a*, 20 *b*, 20 *c* and 20 *d* are formed of a substantially hard, stiff, non-elastic material, such as a metal or a hard plastic. However, it is foreseen that at least some of the rodlets 20 *a*, 20 *b*, 20 *c* and 20*d* may be elastic, flexible, or otherwise deformable. It is noted that, while individual rodlets 20*a*, 20*b*, 20*c* and 20*d* may be somewhat bendable or deformable due to their thinness, when grouped together the rodlets convey strength, rigidity and resilience to the rod portion 12 while simultaneously retaining a small degree of flexibility and a capacity to absorb and/or transmit forces applied thereto.

While in the illustrated embodiment, all of the rodlets 20 have the same cylindrical geometry, including the same diameter and smooth, cylindrical surfaces, it is foreseen that some or all of the rodlets 20 may vary in geometric shape, especially in diameter, and/or material of fabrication so as to provide various desired levels of rigidity to the rod portion 12. For example, a more rigid rod portion 12 may include harder rodlets, while a less rigid rod portion 12 may include more flexible rodlets.

The rodlets 20*a*, 20*b*, 20*c* and 20*d* may be made from may be made of a variety of materials ranging from deformable plastics to hard metals, depending upon the desired application. Suitable materials include, but are not limited to metals, metal alloys and deformable and less compressible plastics, including, but not limited to stainless steel, titanium, titanium alloys and cobalt chrome; and plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers. It is foreseen that in some embodiments, some or all of the rodlets 20*a*, 20*b*, 20*c* and 20*d* may be deformable and/or of a different cross-sectional geometry. Further, it is foreseen that the geometry and fabrication material of the individual rodlets 20*a*, 20*b*, 20*c* and 20*d* may be varied such that, when bundled together, the rod portion 12 is provided a desired level of rigidity or flexibility.

As shown in FIG. 5, the rodlets 20*a*, 20*b*, 20*c* and 20*d* include a substantially circular cross-section with substantially equal diameters, and are spaced relative to one another. The rodlets 20*a*, 20*b*, 20*c* and 20*d* may be joined together using various techniques, structures and/or means. For example, the rodlets 20*a*, 20*b*, 20*c* and 20*d* may be fused together, such as by heat, compression or friction welding, or even by wrapping with a strand or thread-like structure. In other circumstances, a binding material 22, such as an adhesive or an elastomer may join the rodlets 20*a*, 20*b*, 20*c* and 20*d* together. For example, the rodlets 20*a*, 20*b*, 20*c* and 20*d* may be embedded in a polymer material or matrix, such as but not limited to plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

Additionally or alternatively, a plurality of filamentous structures at least partially surround and/or hold and/or bind the rodlets, so as to impart increased tensile strength and resiliency to the rod portion 12. In FIG. 5, exemplary filamentous structures are denoted by the numerals 24*a*, 24*b*, 24*c* and 24*d*. The filamentous structures 24*a*, 24*b*, 24*c* and 24*d* are somewhat flexible, bendable or otherwise deformable threads, fibers, fibrils or microfibers of various lengths, cross-sectional shapes and diameters. The filamentous structures 24*a*, 24*b*, 24*c* and 24*d* randomly bend about the rodlets 20*a*, 20*b*, 20*c* and 20*d*, so as to form a non-woven, tangled, mesh-like structure that secures the rodlets 20*a*, 20*b*, 20*c* and 20*d* and strengthens the rod portion 12. Filamentous structure 24*a*, 24*b*, 24*c* and 24*d* having a wide range of dimensions are foreseen. Further, instead of being randomly tangled, it is foreseen that some or all of the filamentous structures 24a, 24b, 24c and 24d may be elongate and aligned with the rodlets 20a, 20b, 20c and 20d.

The filamentous structures 24a, 24b, 24c and 24d may be fabricated of a variety of materials, such as but not limited to polymers and minerals. Suitable polymers include but are not limited to plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers. Suitable minerals include carbon and certain metals.

It is noted that in some circumstances, the filamentous structures 24a, 24b, 24c and 24d are the binding material 22; no adhesive or elastomeric binder is included. In other circumstances, the binding material 22 is a blend of a base polymer with a plurality of filamentous structures 24a, 24b, 24c and 24d distributed therein. For example, a binding material 22 of a polycarbonate-urethane elastomer and carbon fibers may secure the rodlets 20a, 20b, 20c and 20d together, so as to form the core 18 of the rod portion 12.

The cord portion 14 extends longitudinally from the transition portion 10 to the second end 8. The cord portion 14 is substantially cylindrical with a smooth outer surface. The cord portion 14 includes substantially circular cross-section and a substantially uniform, or constant, diameter along its length, the diameter being sufficient to be received by the bone anchor(s) 4. It is noted that the diameter, or width, of the cord portion 14 is generally less than or equal to the diameter of the rod portion 12. However, in some circumstances, the diameter of the cord portion 14 may be greater than the diameter of the rod portion 12. It is foreseen that the cord portion 14 may have other forms, including but not limited to oval, square and rectangular cross-sections as well as other curved or polygonal shapes.

The cord portion 14 is strong and flexible, elastic or deformable. The cord portion 14 includes a length sufficient for engagement by at least one, two or more bone attachment members 4, and may be cut to the desired length during implantation. Optionally, the cord portion 14 includes an additional tapered portion, located at the second end 8. Such a tapered portion may ease threading the second end 8 through the eye of a closed headed bone anchor 4, tensioning thereof, and subsequently cut off after completion of implantation of the assembly 1.

The cord portion 14 may be made from a variety of materials, including polyester or other plastic fibers, strands or threads, such as polyethylene-terephthalate. A cord according to the invention typically does not illustrate elastic properties, such as any significant additional axial distraction and lengthening after the assembly 1 is operatively assembled and the cord portion 14 is tensioned. However, it is foreseen that in some embodiments, the cord portion 14 may be made of an elastic or semi-elastic material, such as a plastic or rubber (natural or synthetic) having at least some elastic properties, allowing for some further distraction of the assembly 1 during operation thereof. The cord portion 14 can also be a cable-like structure made of metal. Suitable hinged and fixed bone attachment members 4 for mating with the cord portion 14, or with the rod portion 12, are described in Applicant's U.S. patent application Ser. No. 11/328,481 filed Jan. 9, 2006, Publication No. 20060111715, incorporated by reference herein.

The cord portion 14 includes a plurality of substantially flexible, resilient strands. Exemplary strands are denoted by the numerals 26 a, 26 b, 26 c and 26 d. The strands 26 a, 26 b, 26 c and 26 d may be fabricated from a variety of materials having various degrees of elasticity, depending upon the application. Suitable materials include but are not limited to a polymer, such as polyester or other plastic fibers, strands or threads, such as polyethylene-terephthalate. In some circumstances, the strands 26 a, 26 b, 26 c and 26 d are fabricated from substantially elastic or deformable polymers, such as but not limited to natural or synthetic elastomers such as polyisoprene (natural rubber), and synthetic polymers, copolymers, and thermoplastic elastomers, for example, polyurethane elastomers such as polycarbonate-urethane elastomers. In certain embodiments, the strands 26 a, 26 b, 26 c and 26 d are formed of a metal or metal alloy, such as but not limited to stainless steel, titanium, titanium alloys, and carbon.

Alternatively or additionally, some or all of the strands 26 a, 26 b, 26 c and 26 d may be formed of an extruded or spun mixture of a base polymer with polymer or mineral fibers, fibrils or filaments. In an exemplary embodiment, the strands 26 a, 26 b, 26 c and 26 d are fabricated by extruding and curing a mixture of carbon fibers or filaments, and a polymer binder, including but not limited to plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers. It is foreseen that including strands formed of various materials may provide a cord portion 14 with unique characteristics, such as strength, resilience, deformability, flexibility and/or rigidity.

The strands 26 a, 26 b, 26 c and 26 d may be woven, braided, coiled, twisted, plaited, bonded or otherwise joined to grouped together, so as to form the strong and flexible cable, cord or rope of the cord portion 14. Alternatively, as shown in FIG. 6, the strands 26 may be randomly arranged, and optionally bonded, so as to form a somewhat tangled mass, non-woven web or matrix, or similar grouping. In some embodiments, the strands 26 a, 26 b, 26 c and 26 d are embedded in an elastomer, such as described above with respect to the binding material 22 and/or the strand fabrication material, above.

In some embodiments, the cord portion 14, or the strands 26 a, 26 b, 26 c and 26 d, simply abuts the rod portion 12 at the transition portion 10. In other embodiments, strands 26 a, 26 b, 26c and 26 d are extensions of the filamentous structures 24a, 24b, 24c and 24d. For example, the filamentous structures 24a, 24b, 24c and 24d may be strands 26 a, 26 b, 26 c and 26 d that extend from about the first end 6 of the connecting member 2, through the transition portion 10, and to about the second end 8.

In an exemplary embodiment, each strand 26 a, 26 b, 26 c and 26 d includes a length about equal to the length of the connecting member 2. A first portion, of each of the strands 26 a, 26 b, 26 c and 26 d, is aligned, interspersed and bundled with the rodlets 20a, 20b, 20c and 20d, and optionally fused and/or embedded in the binding material 22. The second portion, of each of the strands 26 a, 26 b, 26 c and 26 d, extends from the rod portion 12, past the transition portion 10, and to about the second end 8 of the connecting member 2. The strand second portions may be braided, twisted, plaited, bonded and/or embedded in a polymer, such as into a strong cord-like or cable-like structure, such as described elsewhere herein.

A flexible jacket portion 16 is disposed over and optionally attached to the rod and cord portions 12 and 14 of the connecting member 2. The jacket portion 16 is preferably very strong, flexible and resistant to fraying and degradation during the operable lifetime, or the duration of implantation, of the connecting member 2. Generally, the jacket portion 16 is a woven layer snugly covering the connecting member 2. However, it is foreseen that the jacket portion 16 may be a non-woven layer, such as a tangled mesh of fibers or a polymer film. The jacket portion 16 may be joined, tightly bound or adhered to the connecting member 2, such as by an adhesive or by heat or pressure welding. Alternatively, the jacket portion 16 may be so tightly woven or otherwise formed around the rod and cord portions 12 and 14 that movement of the jacket portion 16 with regards to the rod and cord portions 12 and 14 is substantially blocked The jacket portion 16 may be fabricated of a variety of strong, flexible materials. In order to have low or no wear debris, the jacket outer surface may be coated with an ultra thin, ultra hard, ultra slick and ultra smooth coating, such as may be obtained from ion bonding techniques and/or other gas or chemical treatments. Cooperating portions of an engaging attachment member 4 may also be coated with the ultra thin, ultra hard, ultra slick and ultra smooth coating.

Figure 2:
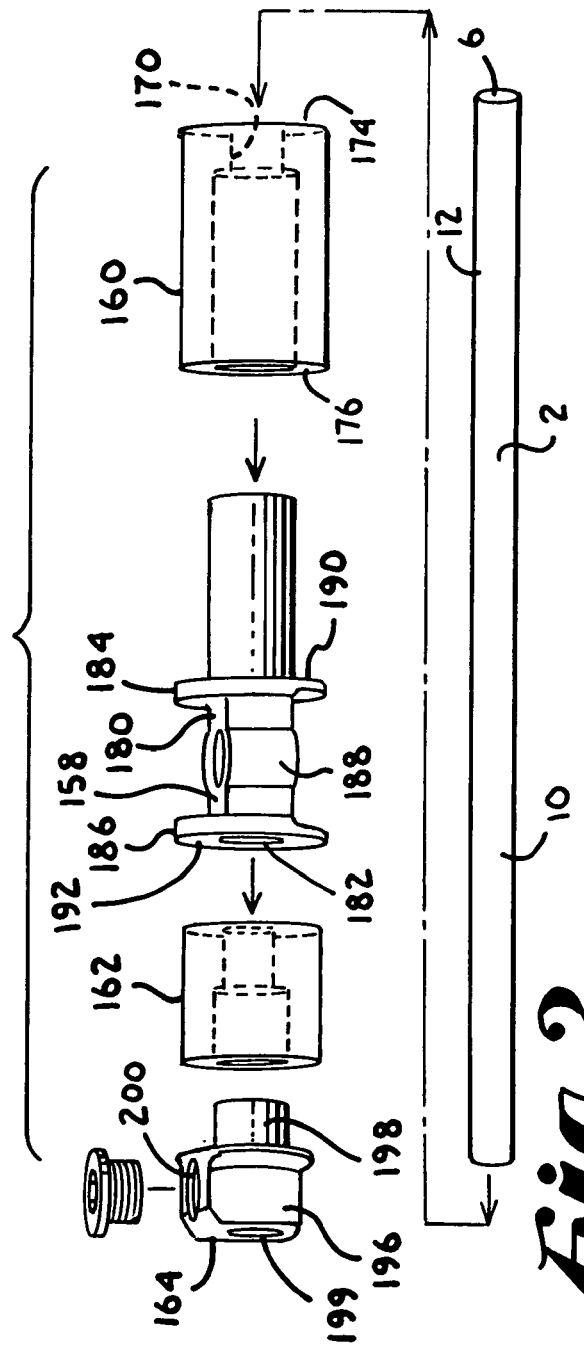
FIG. 2 is an exploded, reduced front elevational view of the dynamic fixation longitudinal connecting member assembly of FIG. 1 shown without the polyaxial bone screws, the assembly including a dynamic fixation longitudinal connecting member having rod and cord portions, an elastic spacer, a rigid sleeve, an elastic bumper, and a cord blocker with set screw.

With reference to FIGS. 1-3, a dynamic stabilization longitudinal connecting member 2 according to the invention is shown attached to three polyaxial bone screws, generally 4. The connecting member 2 is elongate and substantially cylindrical, having a substantially central longitudinal axis A. On the right-hand side of FIG. 1, a first polyaxial bone screw 4 engages the rod portion 12 of the connecting member 2 so as to be located adjacent to the first end 6 thereof. A second, or middle, engaging polyaxial bone anchor 4 is located between the first bone anchor 4 and the transition portion 10. The third, or left-hand, engaging polyaxial bone anchor 4 is located to the left of the transition portion 10 and adjacent to the second end 8. It is noted that the transition portion 10 is not directly engaged by a bone anchor 4. Instead, the transition portion 10 is located between two bone anchors 4.

Initially, one or both of the rod and cord portions 12 and 14 may be substantially longer than required in the completed implant assembly 1, or as shown in FIGS. 1-3. For example, one or both of the rod and the cord portions 12 and 14 may include a length sufficient for engagement by 2, 3, 4 or more bone anchors 4. Additionally, one or both of the rod and cord portions 12 and 14 may include an extra length for grasping with a tool and tensioning the connecting member 2. In some circumstances, such and extension is tapered, to aid in threading the rod or cord portion 12 or 14 through a bone anchor 2, and the like. Accordingly, the rod and cord portions 12 and 14 may be cut to desired lengths during an implantation procedure.

Because the connecting member 2 is substantially solid and cylindrical, it may be used with a wide variety of bone anchors already available for cooperation with rigid rods including fixed, monoaxial bone screws, hinged bone screws, polyaxial bone screws, and bone hooks and the like, with or without compression inserts, that may in turn cooperate with a variety of closure structures having threads, flanges, or other structure for fixing the closure structure to the bone anchor, and may include other features, for example, break-off tops and inner set screws. The bone anchors 4, closure structures and the connecting member 2 are then operably incorporated in an overall spinal implant system 1 for correcting degenerative conditions, deformities, injuries, or defects to the spinal column of a patient. Several suitable hinged and fixed bone screws 4 for mating with the connecting member 2 of the present invention are described in Applicant's U.S. patent application Ser. No. 11/328,481 filed Jan. 9, 2006, Publication No. 2006-0111715; U.S. patent application Ser. No. 12/661,042 filed Mar. 10, 2010; and U.S. patent application Ser. No. 61/336,991 filed Jan. 28, 2010, each of which is incorporated by reference herein.

Each of the polyaxial bone screws 4 includes a threaded shank 152 for attachment to bone (not shown), a receiver 154 that is adapted to receive the connecting member 2, and a closure top 156 that locks the bone screw 4 into a fixed position. In some circumstances, a slide or slipping closure top 156, with a substantially flat bottom surface 156a is used to slidingly secure connecting member cord portion 14 in the receiver 154. In some circumstances, a non-sliding closure 156 may be employed with the cord portion 14, so as to lock the cord portion in the receiver 154. In other circumstances, a point and rim closure top closure top 156, with a bottom surface 156b having a structure that contacts, grips and fixedly engages the rod portion 12, is used to lock the connecting member rod portion 12 in the receiver 154. A detailed description of these types of closure tops can be found in Applicant's co-pending U.S. patent application Ser. No. 12/661,042 filed Mar. 10, 2010, incorporated herein by reference.

In addition to the bone screws 4 and the connecting member 2, the illustrated connecting member assembly 1 generally includes at least a hard, inelastic flanged sleeve 158, an elastic spacer 160, an optional rigid spacer liner (not shown), an elastic bumper 162 and a cord blocker 164 with cooperating set screw 168. A detailed description of these structures can be found in Applicant's U.S. patent application Ser. No. 61/336,991 filed Jan. 28, 2010, incorporated herein by reference.

Referring to FIGS. 2-3, the connecting member 2 extends along the axis A, from the first end 6 to the second end 8, and successively through and within the first and second bone anchors 4, the spacer 160, the sleeve 158, the third bone anchor 4, the bumper 162 and the cord blocker 164, for example. As best shown in FIG. 3, the connecting member transition portion 10 is located between two bone screws 4, so as to not be directly engaged by a bone screw 4. In the illustrated embodiment, the transition portion 10 is located between the second and third bone anchors 4, as well as within both the sleeve 158 and the spacer 160.

It is noted that in some circumstances, one or both of the rod and cord portions 12 and 14 may be longer than depicted in FIGS. 1-3. Accordingly, a suitable number of additional spacers 160, sleeves 158, and/or bone anchors 4 would be employed with the cooperating connecting member 2. For example, the rod portion 12 may include a length sufficient for engagement by three or more bone anchors 4. Similarly, the cord portion 14 may include a length sufficient for engagement by two or more bone anchors 4, including a suitable number of cooperating sleeves 158 and spacer 160. It is noted that, in some circumstances, a non-sliding closure 156 may be employed cooperatively with a sleeve 158, so as to block sliding axial movement of the sleeve 158 relative to the core portion 14.

The spacer 160 is substantially elastic, longitudinally extending, cylindrically shaped, with a smooth outer surface 169. The spacer 160 is typically elastic and made from a plastic, for example, a thermoplastic elastomer made from a polyurethane or polyurethane blend, such as a polycarbonate urethane. The spacer 160 is adapted to be cut to length by the surgeon.

The spacer 160 includes a substantially cylindrical through-bore 170 with a smooth inner surface 172 that extends from a first end 174 of the spacer 160 to a second end 176 thereof. The through-bore 170 is sized and shaped so as to receive the connecting member 2 therethrough. The through-bore 170 diameter is at least slightly greater than that of the connecting member 2, such that the connecting member 2 may be received therethrough. In some circumstances, the spacer inner surface 172 contacts an outer surface 178 of the connecting member 2. In other circumstances, the through-bore 170 diameter is sized such that the spacer inner surface 172 is spaced from the connecting member outer surface 178. In some circumstances, at least a portion of the through-bore 170, or the inner surface 172, is sized and shaped, or graduated, so as to also receive therein at least one of an optional liner (not shown) and a portion of the sleeve 158, such as described below. The spacer 160 may include various and graduated inner surfaces 172 that are sized and shaped to be press fit over a knobbed feature of an adjacent sleeve or a liner (not shown).

In the completed assembly 1, the connecting member 2 is received through the spacer through-bore 170 such that the transition portion 10 is located within the spacer 160. The spacer first end 174 is planar and annular, and abuts the receiver 154 of the second, or middle, bone anchor 4. The spacer second end 176 is also planar and annular, and abuts the receiver 154 of the third bone anchor 4 and/or the sleeve 158 covering the cord portion 14, such as described below. In some circumstances, the ends 174 and 176 are non-planar and contoured so as to cooperatively matingly engage the side of the bone anchor receiver 154.

A sleeve 158 is received over, or about, the cord portion 14, so as to be located between the cord portion 14 and the bone anchor receiver 154, so as to protect the cord portion 14 from crushing and degradation. The sleeve 158 includes a body 180, a longitudinally extending through-bore 182, two flanges 184 and 186, a centering body portion 188 between the flanges 184, and a closure-receiving orifice 183 joining the top surface of the centering body 188 with the interior surface of the through-bore 182. The end surfaces 190 and 192 of the sleeve 158 may substantially planar and annular, or they may sized and shaped, or contoured, so as to cooperatively matingly engage the bone anchor receiver 154. Optionally, the sleeve 158 includes a tubular extension 193 that extends partially into and/or through the spacer through-bore 170. Additionally, or alternatively to the tubular extension 193, the sleeve 158 may include a knobbed structure (not shown) disposed adjacent to the flange 186 and/or the flange 184. Such a knobbed structure provides a push-on connective element for attachment to inner graduated surfaces of the spacer 160 and/or the bumper 162.

It is noted that more than one size of sleeve 158 is typically provided to the surgeon, the sleeves 158 differing only in the length of the tubular extension 193 included, so as to appropriately match the size of the patient's spine. A desirable fabrication material for both the optional liners and the sleeve tubular extensions 193 is cobalt chromium. Furthermore, in some embodiments of the invention, in order to have low or no wear debris, the liner inner surface and the outer surfaces of the sleeve tubular extensions 193 may be coated with an ultra thin, ultra hard, ultra slick and ultra smooth coating, such as may be obtained from ion bonding techniques and/or other gas or chemical treatments. It is further noted that sleeve inner surfaces 194 may also be likewise coated to provide a slick, low to no wear debris interface with the cord portion 14.

Referring to FIG. 3, the connecting member cord portion 14 is received through the through-bore 182 and is secured or locked with a slide or slipping closure top 156. The closure top 156 also fixedly locks the sleeve 158 in the bone screw 4. The slide or slip closure top 156 engages the sleeve 158 but not the cord portion outer surface 178, allowing the cord portion 14 to slip or slide within the polyaxial screw 4. It is foreseen that a grip closure top 156 may be used in place of a slip closure top 156. A grip closure top extends through the sleeve 158 and grips and fixes the cord portion 14 against an inner surface 194 of the sleeve 158 and thus fixes the cord portion 14 in relation to the polyaxial screw 4.

A portion of the sleeve 158 may extend into and through the spacer 160 and is in slidable relationship therewith. Such spacer overlap with respect to the sleeve 158 provides advantageous anti-shear support for the connector 2. A portion of the cord blocker 164 also extends into a bore of the bumper 162. The bumper 162 is typically made from an elastomer while the spacer 160, although typically elastomeric, may be made from a material with a different durometer, typically (but not always) being tougher and less compressible than the material of the bumper 162. The sleeve 158 and the optional spacer liner are made from a hard, non-elastic material, such as a metal or metal alloy, like cobalt chromium. The hard and stiff sliding sleeve 158 may include an extension that slides into the respective liner, providing a dynamic no- or low-wear, sliding relationship between the sleeve and optional cooperating liner that is non-binding, and provides excellent shear resistance. At the same time, the thin liner and the cooperating elastomeric spacer 160, as well as the tensioned cord portion 14, provide controlled bending, with the tensioned cord portion 14 and compressed bumper 162 performing well under tension and compression. The flanged portions 184 and 186 of the sleeve 158 are located on either side of the bone screw receiver 154, the flange surfaces 190 and 192 abutting against the spacer 160 and the bumper 162, the flanges 184 and 186 extending radially outwardly to an extent to fully engage the ends of the adjacent spacer 160 or the bumper 162, resulting in a stable, secure, substantially full contact between the individual elements of the assembly 1. Furthermore, the flanges 184 and 186 allow for assembly and dynamic setting of the assembly 1 prior to implantation, if desired, with the cord portion 14 being placed in tension and at least the bumper 162 being placed in compression. In some embodiments of the invention, tensioning of the cord portion 14 and compression of the bumper 162 and optionally the spacer 160 may be performed after the assembly 1 is attached to the bone screws 4.

The bumper 162 is elastic and may be made from a variety of compressible and stretchable materials, including, but not limited to natural or synthetic elastomers such as polyisoprene (natural rubber), and synthetic polymers, copolymers, and thermoplastic elastomers, for example, polyurethane elastomers such as polycarbonate-urethane elastomers. In order to have low or no wear debris, the bumper inner surface may also be coated with an ultra thin, ultra hard, ultra slick and ultra smooth coating, such as may be obtained from ion bonding techniques and/or other gas or chemical treatments.

With particular reference to FIGS. 13-16, the cord blocker 164 and cooperating set screw 168 are shown. The cord blocker 164 includes a body portion 196 and a tubular extension 198 sized and shaped to be slidingly received in the bumper 162. The illustrated body portion 196 and tubular extension 198 are integral or otherwise fixed to one another. A through-bore 199 extends through a lower portion of the body portion 196 and centrally through the tubular extension 198. The through-bore 199 is sized and shaped to receive the cord portion 14 and when assembled with a remainder of the assembly 1 extends along the axis A. The body portion 196 includes an outer side and lower surface 166 that is substantially U-shaped in cross-section, however, the lower surface 166 may have a variety of outer geometries, including cylindrical or of other curved or polygonal cross-sections. The lower surface 166 terminates at an upper planar surface 167. Formed in the body portion 196 is a threaded bore 200 sized and shaped to receive and threadably mate with a thread of the cooperating set screw 168. The threaded bore 200 communicates with the through-bore 199 and is substantially perpendicular thereto. Near the intersection of the through-bore 199 and the threaded bore 200, a surface 173 partially defining the through-bore 199 includes a depression 175, sized and shaped for receiving the cord portion 14 therein when the set screw 168 engages the cord portion 14. The sleeve 160 also includes such a depression for receiving the cord portion 14 within the through-bore 182 thereof when the grip closure top 165 is used to clamp the cord portion 14 within the sleeve 160 without damaging or destroying the cord portion 14. The cord blocker 164 further includes opposed substantially planar end surfaces 177 and 179. The end surface 177 is also the end surface of the tubular extension 198 that has an outer cylindrical surface 181. The end surface 179 is also the end surface of the body portion 196. The body portion 196 further includes a substantially annular planar end surface 183 adjacent the tubular extension 198. In operation, an end surface of the bumper 162 abuts against the end surface 183.

It is noted that the blocker 164 and set screw 168 combination is typically provided with the bumper 162 pre-attached thereto and handled as a unit assembly. Thus, prior to being received by the surgeon, the bumper 162 is wedged and in some cases adhered or otherwise fixed onto the tubular extension 198 at the factory, with the inner surface of the bumper frictionally engaging the outer surface of the tubular extension 198 and the bumper 162 abutting against and fixed to the blocker body 196.

Various closure tops 156 may be used with the bone anchors 4. Suitable closure tops 156 include a break-off head designed to allow such a head to break from a base of the closure at a preselected torque, for example, 70 to 140 inch pounds. The closure structure 156 generally includes an outer helically wound guide and advancement structure (not shown) that is sized and shaped to rotatably mate with a cooperating inner helically wound guide and advancement structure (not shown) on the bone screw receiver 154. The bottom surface of the closure top 154 may be either include a point and rim or be substantially planar. A smooth or flat bottom surface 156a is designed to not grip and fixedly engage the connecting member 2, so as to allow sliding of the connecting member 2 within the bone screw receiver 154. A point and rim bottom surface 156b is designed to grip and fixedly engage the connecting member 2, so as to block sliding of the connecting member 2 within the bone screw receiver 154.

The assembly 1 may be assembled as follows: First, after the bone screws 4 are implanted, the distance between the screws is measured. Thereafter, the spacer 160, and optional liner, is cut to a desired length based upon the measurement made between the bone screws. A tool (not shown), similar to a pipe cutter, is usually used to rotate and cut the spacer 160 to the desired length at an end opposite the optional graduated surfaces of the spacer. Also at this time, in view of the resulting spacer length, a cooperating sleeve 158 of desired size is chosen. Because the sleeve 158 is made from a hard material, typically a metal or metal alloy, it is not practical to cut the tube portion 193 to a desired length during the surgical procedure. Therefore, a variety of sleeves 158 are typically provided to end users having at least three different tube portion lengths.

With particular reference to FIG. 2, the cord portion 14 is then successively threaded through the connector elements as shown by the arrow G in FIG. 2, some of the components, such as the blocker/bumper 164/162 having been previously assembled. As the cord portion 14 is threaded into the assembly elements, the spacer 160 is placed into position covering or overlapping the optional tubular portion 193 of the sleeve 158. The cord portion 14 is typically much longer than shown in FIG. 2 and then cut to length near the end 8 after being fully assembled with the remaining elements of the assembly 1, so that the cord portion 14 may be grasped and tensioned either before or after the assembly 1 is fixed to the bone screw 4. If pre-tensioning is desired, at this time, prior to implanting the assembly, a tensioning tool (not shown) known in the art is used to pull upon and put tension on the cord portion 14 near the end 8. The cord portion 14 is preferably tensioned until the bumper 162 compresses and then the set screw 168 is rotated and driven into the blocker 164 and up against the cord portion 14 using a driving tool (not shown) engaged with an inner drive of the set screw 168. The blocker 164 advantageously includes opposed planar sides allowing for the placement of a counter-torque tool (not shown) for holding the blocker 164 during tensioning and fixing of the cord portion 14 within the blocker 164.

The assembly 1 (either pre-tensioned or in a loosely attached orientation) is implanted by inserting the sleeve body portions into the bone screws 4 with each receiver 10 being received between the two flanges of the sleeve 158. Closure tops 156 are chosen by the surgeon based upon whether a sliding or a gripping relationship is desired with the particular receiver 154.

With reference to FIG. 1, the final tensioned assembly 1 is shown that is substantially dynamically loaded and oriented relative to the cooperating vertebra, providing relief (e.g., shock absorption) and protected movement with respect to flexion, extension, distraction and compressive forces placed on the assembly 1 and the connected bone screws 4 as well as providing more rigid support at the rod portion 12. During complex spinal movements, the spacer 160 is able to move or flex away from and towards the flange 184 of the sleeve 158 without compromising the strength and integrity of the assembly 1. It is noted that a problem encountered with dynamic spinal implant systems is the need to provide adequate support with respect to bending sheer. Most spinal movements are not purely bending movements, e.g., flexion and extension. Most movements include both bending and tension, extension or compression. Such bending shear is not well resisted by a cord and spacer alone that performs well in tension, but not when the tension includes a vector force. The present invention advantageously provides a hard, non-elastic extension of a rigid sliding sleeve body 180, the optional extension further located within a optional non-elastic liner of the spacer 160. Such features protect against vector forces while still allowing for advantageous tension of the cord portion 14 as well as improved compression provided by the outer bumper 162. The cord portion 14 and the sleeve 158 allow for some twisting or turning, providing some relief for torsional stresses. Furthermore, the compressed bumper 162 and the fixed contact between the sleeve 158 and the end of the spacer 160, as well as the fixed contact between the bumper 162 and the blocker 164 places some limits on torsional movement as well as bending movement, to provide spinal support. The cord portion 14 (in tension) and bumper 162 (in compression) allow for compression and some extension of the assembly 1 located between the two bone screws 4, e.g., shock absorption. Another advantage of embodiments of the present invention is that because of the inelastic sleeve extension 193 that slides within and is overlapped by the typically elastic spacer 160 located between two bone screws 4, the resulting assembly 1 is more stable than a cord portion 14 and spacer 160 alone, therefore strength of the assembly 1 does not rely upon the amount of tension placed upon the cord portion 14. Therefore, in embodiments according to the invention, it is not necessary to place as much tension on the cord portion 14 as would be required for a more traditional cord and spacer arrangement, thus protecting the cord from damage of over stressing.

If removal of the assembly 1 from any of the bone screw assemblies 4 is necessary, or if it is desired to release the assembly 1 at a particular location, disassembly is accomplished by using the driving tool (not shown) with a driving formation cooperating with internal drives of the closure structures 156, to rotate and remove such closures from the receivers 154. Disassembly is then accomplished in reverse order to the procedure described previously herein for assembly.

Eventually, if the spine requires more rigid support, the connecting member 2 according to the invention may be removed and replaced with another longitudinal connecting member, such as a solid rod or bar, having the same width or diameter as body portion 196 of the sleeve 158, utilizing the same receivers 154 and the closure structures 156. Alternatively, if less support is eventually required, a less rigid, more flexible assembly, for example, an assembly 1 having spacers and bumpers made of a softer more compressible material than the spacers and bumpers being replaced thereby, also utilizing the same bone screws 4.

FIG. 6 illustrates another embodiment of the dynamic longitudinal connecting member, generally 102. The connecting member 102 is substantially identical to the connecting member 2 described above, with the exception that it includes two cord portions joined by a rod portion. Accordingly, the description of the connecting member 2 is incorporated herein by reference.

The connecting member 102 extends longitudinally along a central axis B, from a first end 106 to a second end 108, with first and second transition portions 110 a and 110 b located therebetween. The connecting member 102 includes three portions, namely a rod portion 112 that joins a first cord portion 114 a with a second cord portion 114 b. A jacket portion 116 covers the rod and cord portions 112, 114 a and 114 b, similar to the jacket portion 16 described above. The length of the connecting member 102 is sufficient for engagement by at least three bone attachment members 4, such as those described above. Typical arrangements of the connecting member 102 include but are not limited to a rod portion 112 with a length sufficient for engagement by one, two, three or more bone anchors 4, joining first and second cord portion 114 a and 114 b, each cord portion including a length sufficient for engagement by one, two, three or more bone anchors 4. In an exemplary embodiment, the rod portion 112 includes a length sufficient for engagement by a single bone anchor 4, and the first and second cord portion 114 a and 114 b each include a length sufficient for engagement by either one or two bone anchors 4. In another exemplary embodiment, the rod portion 112 includes a length sufficient for engagement by two bone anchors 4, and the first and second cord portion 114 a and 114 b also each include a length sufficient for engagement by two bone anchors 4. Additional combinations of rod and cord portion 112, 114 c and 114 b lengths is foreseen.

The connecting member 102 is substantially cylindrical with one or more circular cross-sections along a length thereof. However, it is foreseen that the connecting member 102 may have other forms, including but not limited to oval, square and rectangular cross-sections as well as other curved or polygonal shapes.

The diameter of the connecting member 102 is uniform along its entire length, and sufficient for engagement by the attachment members 4. However, as described above, the cord portions 114 a and 114 b may include optional tapered portions or extension that may aid in the implantation procedure. Such tapered extensions are typically removed when the cords 114 a and 114 b are cut to the final length.

The rod portion 112 is substantially identical to the rod portion 12 of the connecting member 2, with the exception that rod portion 112 extends from the first transition portion 110 a to the second transition portion 110 b. The rod portion 112 includes a plurality of rodlets 120 fabricated as described above with reference to the rodlets 20, and which may be joined together by a binding material and/or by filamentous structures similar to those described above. The rod portion 112 is substantially rigid, cylindrical and smooth, and includes a length sufficient for engagement by at least one, preferably at least two bone attachment members 4, such as described elsewhere herein.

The first cord portion 114 a is substantially identical to the cord portion 14 of the connecting member 2, with the exception that the first cord portion 114 a extends from the first end 106 to the first transition portion 110 a. The first cord portion 114 a includes a plurality of strands 126 fabricated as described above with reference to the strands 26. The first cord portion 114 a is substantially flexible, cylindrical and smooth, and includes a length sufficient for engagement by at least one, preferably at least two bone attachment members 4, such as described elsewhere herein. The first cord portion 114 a may be cut to length during implantation by the surgeon.

The second cord portion 114 b is substantially identical to the first cord portion 114 a and to the cord portion 14 of the connecting member 2, with the exception that the second cord portion 114 b extends from the second transition portion 110 b to the second end 108. The second cord portion 114 b includes a plurality of strands 126 fabricated as described above with reference to the strands 26. The second cord portion 114 b is substantially flexible, cylindrical and smooth, and includes a length sufficient for engagement by at least one, preferably at least two bone attachment members 4, such as described elsewhere herein. Similar to the first cord portion 114 a, the second cord portion 114 b may include an extra length and/or optional tapered portion for manipulating the connecting member 102 during the implantation procedure 102, and may be cut to length during implantation by the surgeon.

The cord portions 114 a and 114 b may be joined with the rod portion 112 in various ways. In an exemplary embodiment, the bundled strands 126 of the first and/or second cord portions 114a and/or 114 b may abut and be secured to the rod portion 112, such as at the transition portions 110 a and 110 b, respectively. In another exemplary embodiment, the strands 126 extend into and optionally through the rod portion 112. For example, the strands 126 of the first portion 114 *a* may extend from the first end 206, through the first transition portion 110 *a*, and at least partially through the rod portion 112. In some circumstances, the strands 126 may extend all of the way through the rod portion 112, from the first end 206 to the second transition portion 110 *b*; such that the strands 126 of the first cord portion 114 *a* are also the strands 126 of the second portion 114 *b*. In still other circumstances, the strands 126 extend all the way, from the first end 206 to the second end 208. And, in yet another example, the strands may extend through the second cord portion 114*b*, from the second end 208 to the transition portion 110 *b*, and then at least partially through, the rod portion 112. In some circumstances, the strands 126 may extend all of the way through the rod portion 112, from the second end 208 to the second transition portion 110 *a*. Optionally, the strands 126 of the first and/or second cord portions 114 *a* and/or 114 *b* replace, or are, fibers within the rod portion 112, so as to hold and/or bind the rodlets together.

The jacket portion 116 is substantially identical to the jacket portion 16, the description of which is incorporated herein by reference. The jacket portion 116 extends from the first end 106 to the second end 108 and provides a substantially smooth surface to the connecting member 102. The jacket portion 116 is substantially strong and flexible, able to block substantial fraying over the lifetime of the implant. In some embodiments, the jacket portion 116 is a woven or braided structure. In other embodiments, the jacket portion 116 is a non-woven web of fibers. In still other embodiments, the jacket portion 116 is a tough, resilient membrane deposited on, and optionally bonded to, the connecting member 102. In order to have low or no wear debris, the jacket portion 116 outer surface may be coated with an ultra thin, ultra hard, ultra slick and ultra smooth coating, such as may be obtained from ion bonding techniques and/or other gas or chemical treatments. It is further noted that inner surfaces of sleeves and/or bone attachment members that receive the connecting member 102 may also be likewise coated to provide a slick, low to no wear debris interface with the connecting member 102.

Figure 7:
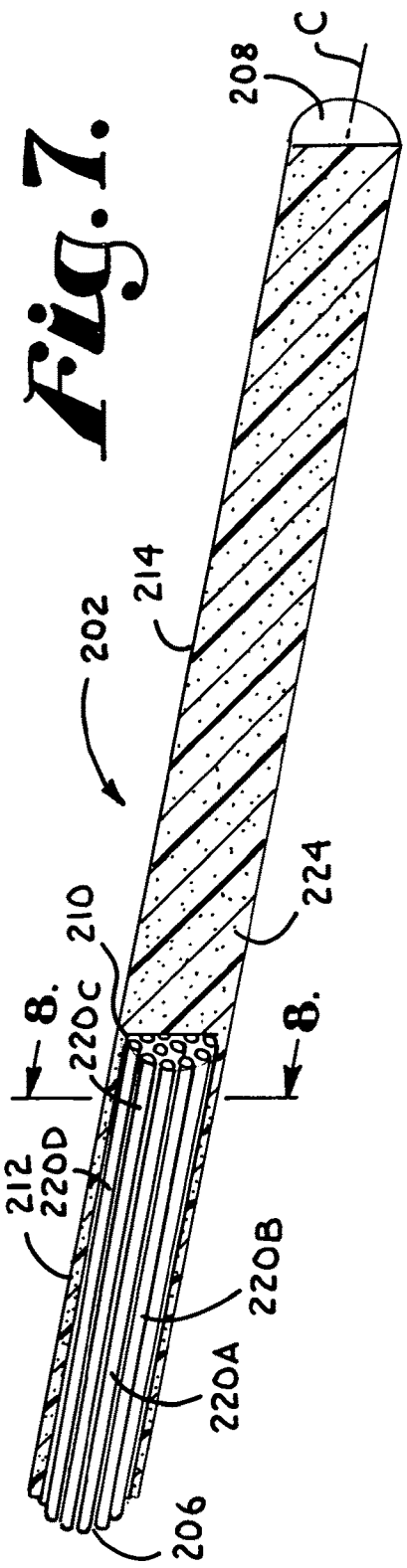
FIG. 7 is a perspective view of a third embodiment of a dynamic fixation longitudinal connecting member according to the invention, including a rigid first rod portion and an elastic second rod portion, with portions broken away to show detail thereof.
Figure 8:
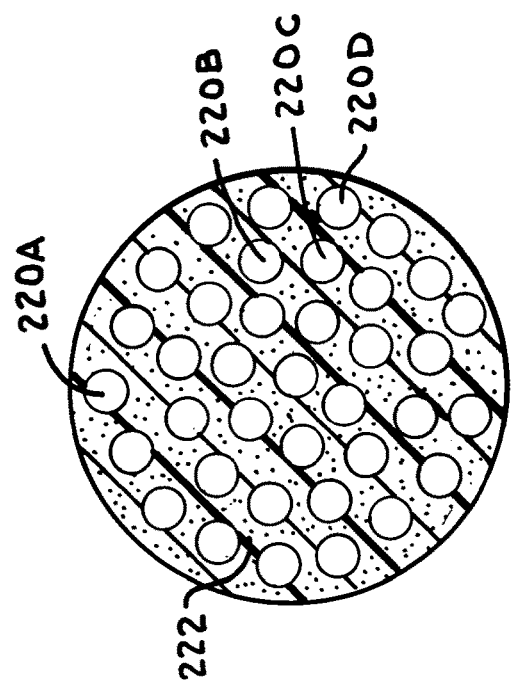
FIG. 8 is an enlarged cross-sectional view of the dynamic fixation longitudinal connecting member of FIG. 7, taken along the line 8-8 of FIG. 7.

FIGS. 7-8 illustrate another embodiment of a dynamic longitudinal connecting member 202 according to the invention. The connecting member 202 is similar to the connecting members 2 and 102, the descriptions of which are incorporated herein by reference.

The connecting member 202 is a longitudinally extending rod-shaped structure, with a longitudinal axis C, first and second end 206 *s* and 208, a transition portion 210, and two rod portions joined at the transition portion 210, a substantially rigid first rod portion 212 and a substantially elastic second rod portion 214. The connecting member length is sufficient for engagement by two or more bone anchors 2. Similar to the connecting member 2, the connecting member 202 is substantially cylindrical, with a circular cross-section. However, it is foreseen that the connecting member 202 may have other forms, including but not limited to oval, square and rectangular cross-sections as well as other curved or polygonal shapes. The diameter of the connecting member 202 is substantially constant or uniform along its length, and sufficient to be matingly engaged by a bone anchor 4, as described elsewhere herein.

The first rod portion 212 is substantially rigid and runs parallel along the axis C, from the first end 206 to the transition portion 210. A plurality of long, thin and cylindrical rodlets, some of which are denoted by the numerals 220A, 220B, 220C and 220D, are aligned with the axis C and extend from the first end 206 to the transition portion 210. The rodlets 220A, 220B, 220C and 220D include a substantially circular cross-section with substantially equal diameters.

The rodlets 220A, 220B, 220C and 220D are fabricated similarly to those of the rod portion 12, such as from a variety of materials ranging in hardness and elasticity from deformable plastics to hard metals, depending upon the desired application. Suitable materials include, but are not limited to metals, metal alloys and deformable and less compressible plastics, including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers. It is foreseen that some or all of the rodlets 220A, 220B, 220C and 220D may be deformable and/or of a different cross-sectional geometry. Further, it is foreseen that the geometry and fabrication material of the individual rodlets 220A, 220B, 220C and 220D may be varied such that, when bundled together, the rod portion 212 is provided a desired level of rigidity or flexibility.

As is most easily seen in FIG. 8, the rodlets 220A, 220B, 220C and 220D are spaced from each other and embedded in a polymer material or matrix 222, such as but not limited to plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers. The polymer is shaped such that an exterior surface 223*a* of the first rod portion 212 is substantially cylindrical and smooth. In order to have low or no wear debris, the exterior surface 223*a* may be coated with an ultra thin, ultra hard, ultra slick and ultra smooth coating, such as may be obtained from ion bonding techniques and/or other gas or chemical treatments.

The second rod portion 214, sometimes referred to the cord portion, is a substantially elastic or deformable polymer rod-like structure running parallel with the axis C, from the transition portion 210 to the second end 208. The second rod portion 214 includes a diameter that is substantially uniform along its length, with the exception of an optional tapered portion at the second end 208. The length of the second rod portion 214 is sufficient for engagement by at least one bone anchor, and generally includes an extra length used by the surgeon during the implantation procedure to grasp and pull the connecting member 202, such as described elsewhere herein.

The second rod portion 214 is formed of an elastomeric polymer material or matrix, similar to the polymer material 222. In some embodiments, the second rod portion 214 and the polymer material 222 are integrally formed. For example, the rodlets 220A, 220B, 220C and 220D may be placed in a mold that is sized for injection molding both the first and second rod portions 212 and 214. The mold is then filled with liquid polymer that is subsequently cured, to yield the completed connecting member 202. Alternatively, the first and second rod portions 212 and 214 may be fabricated separately, abutted together and then joined at the transition portion 210, all steps using known manufacturing techniques.

The second rod portion 214 may be fabricated from a variety of elastic, deformable materials. Suitable materials include but are not limited to plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers. While the second rod portion 214 does not generally include strands, similar to those described above, in some circumstances, the second rod portion 214 does include polymer or mineral fibers, such as described elsewhere herein. Such fibers may strengthen the second rod portion 214, thereby making it better able tow withstand shear and torsional forces.

The second rod portion 214 is formed of a composite of at least two materials. In an exemplary embodiment, thin, longitudinally extending layers of two or more polymers of differing durometers may be fused together to provide increased strength or varying flexibility to the second rod portion 214. A similar effect may be achieved by fusing together thin rods of two or more polymers of differing durometers. In another exemplary embodiment, polymers of different durometers may be used along the length of the second rod portion 214, either as discreet layers or as a continuous transition from one polymer to the next, so as to vary or change the relative rigidity, hardness, flexibility and/or deformability of the second rod portion 214 along its length. In yet another exemplary embodiment, concentric layers of two or more polymers may be formed into the second rod portion 214, such as by alternately or successively applying, such as by dipping spraying, layers of two or more polymers to a small polymer core structure, with a cure step after each application.

The exterior surface 223b of the second rod portion 214 is shaped so as to be substantially cylindrical and smooth. In order to have low or no wear debris, the exterior surface 223b may be coated with an ultra thin, ultra hard, ultra slick and ultra smooth coating, such as may be obtained from ion bonding techniques and/or other gas or chemical treatments.

While not shown, the connecting member 202 of the invention may be used with the same or similar spacers and/or sleeves with cooperating closure, as described above with respect to the connecting member 2, especially to protect the transition portion 210 and to provide additional support to the elastic portions of the connecting member 202. The transition portion 210 is located between two bone anchors 4. The assembly 1 including the connecting member 202 preferably includes a spacer surrounding the transition portion 202, similar to that described above with regards to FIGS. 1-3.

FIGS. 9-12 illustrate yet another embodiment of a dynamic longitudinal connecting member 302 according to the invention. The connecting member 302 is substantially similar to the connecting members 1, 102 and 202, the descriptions of which are incorporated herein by reference.

The connecting member 302 extends longitudinally along the central axis D, from a first end 306 to a second end 308, with a transition portion 310 located therebetween. Over all, the connecting member 302 is substantially cylindrical, with a circular cross-section and a diameter that is substantially uniform along its length. The connecting member 302 includes a length sufficient for engagement by at least two bone anchors 4. For example, in FIG. 12, the connecting member 302 is shown as engaged by four bone anchors 4. The connecting member 302 may be used in combination with cooperating sleeves and/or spacers, similar to those described above. The connecting member 302 includes two portions, a substantially rigid first rod portion 312 and a substantially flexible, elastic second rod portion 314.

Referring to FIGS. 9-12, the substantially rigid first rod portion 312 extends a length sufficient for engagement by at least one, preferably at least two bone anchors 4, and includes an inelastic stent structure 320 that is at least partially embedded in an elastomeric polymer material 322. The elastomeric polymer material 322 is shaped such that a surface 322A thereof is substantially smooth and uniformly cylindrical along its entire length. Since the length of the first rod portion 312 may be much longer than required in the completed implant assembly 1, is may be cut to length by the surgeon using methods described elsewhere herein.

The stent structure 320 extends along the axis D, from the first end 306 to the transition portion 310. The stent structure 320 includes first and second ends 320A and 320B. The ends 320A and 320B are generally annular and may be planar, outwardly curved or contoured. The stent structure 320 includes a plurality of longitudinally extending concave surfaces 320C joined by ridge surfaces 320D. In an exemplary embodiment according to the invention, the stent structure 320 shown in FIGS. 10 and 11 includes five concave surfaces 320C, wherein adjacent concave surfaces 320C are joined by ridge surfaces 320D. Since the stent structure 320 is embedded in the polymer 322, spaced defined by the concave surfaces 320C and the exterior surface of the connecting member 302 are substantially filled with the elastomeric polymer material 322. The concave surfaces 320C provide an enlarged surface area for tightly binding with the elastomeric polymer material 322, for example, such that there is substantially no slippage between the two structures. The longitudinally extending surfaces 322A of the polymer material 322, which fills the spaces, are convex, outwardly bowed or partially cylindrical.

The ridge surfaces 320D are slightly convex and substantially flush with the outer surface 312a of the first rod portion 312. The surfaces of the polymer material 322 are shaped such that together with the ridge surfaces 320D, a cross-section of the connecting member 302 is circular, thereby providing the cylindrical outer surface of the connecting member 302. However, it is foreseen that the ridge surfaces 320D may be other shapes, such as planar. Further, it is foreseen that the ridge surfaces 320D may be located slightly above or below the outer surface 312A.

Referring now to FIGS. 10-11, due to the alternating arrangement of the concave and ridge surfaces 320C and 320D, the stent structure 320 has a generally star or starfish-shaped cross-section. For example, the illustrated embodiment has a five-armed starfish shaped cross-section. However, it is foreseen that the stent structure 320 could have more or fewer concave surfaces 320C and ridge surfaces 320D, thereby giving the cross-section more or fewer "arms" than are shown in FIGS. 10-11. It is noted that the widest diameter, or width of the cross-section is about equal to the diameter of the connecting member 302.

The stent structure 320 includes a longitudinally extending through-bore 320E, which extends from the first end 320A to the second end 320B. The through-bore 320E is coaxial with the axis D. The through-bore cross-section is substantially circular. However, it is foreseen that the cross-section may have other shapes, such as ovular, rectangular, or even irregular. The through-bore 320E is substantially filled with the elastomeric polymer material 322.

A plurality of spaced perpendicular bores 320F extend radially through the stent structure 320, so as to join the concave surfaces 320C with the lumen, or internal surface, of the through-bore 320E. As shown in FIG. 9, a plurality of perpendicular bores 320F are spaced along the length of each concave surface 320C. Further, the perpendicular bores 320F of a first concave surface 320C are staggered with respect to the perpendicular bores 320F of the adjacent concave surfaces 320C. The perpendicular bores 320F are also substantially filled with the elastomeric polymer material 322, said material 322 being integral with the material 322 filling the through-bore 320E.

The stent structure 320 is embedded in the elastomeric polymer material 322, which fills the spaces of the concave surfaces 320C, the through-bore 320E and the perpendicular bores 320F. The material filling all of these spaces or elements is substantially integrally formed. Suitable polymer materials 322 include but are not limited to plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers. In order to have low or no wear debris, the convex outer surface 312a may be coated with an ultra thin, ultra hard, ultra slick and ultra smooth coating, such as may be obtained from ion bonding techniques and/or other gas or chemical treatments.

The second rod portion 314 is a substantially elastic, substantially cylindrical rod that extends from the transition portion 310 to the connecting member second end 208. The second rod portion 314 has a smooth and convex, or cylindrical, outer surface 314a and a substantially circular cross-section. The diameter of the second rod portion 314 is substantially uniform, or constant, along its entire length, and sufficiently sized such that second rod portion 314 is receivable or engageable by a bone anchor 4. The second rod portion 314 includes a length sufficient for engagement by at least one, preferably at least two bone anchors 5. Generally, the second rod portion 314 is longer than is required in the completed implant assembly 1, and is cut to length by the surgeon. The extra length of the second rod portion 314 may be used by the surgeon in tensioning the second rod portion 314.

The second rod portion 314 is formed of an elastomeric polymer material 322, such as but not limited to plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers. In order to have low or no wear debris, the outer surface 314a, of the second rod portion 314, may be coated with an ultra thin, ultra hard, ultra slick and ultra smooth coating, such as may be obtained from ion bonding techniques and/or other gas or chemical treatments.

In some embodiments, the second rod portion 314 is integrally formed with the material in which the stent structure 320 is embedded, and which therefore fills the concave surfaces 320C, the through-bore 320E and perpendicular bores 320F. In an exemplary embodiment, the connecting member 302 is fabricated by placing the stent structure 320 in an injection mold sized and shaped to form the completed connecting member 302. The mold is filled with a liquid polymer material 322, that is subsequently cured, thereby forming the completed connecting member 302. Alternatively, the first and second rod portions 312 and 314 may be fabricated separately, abutted and joined in the completed connecting member 302.

Referring now to FIG. 12, the connecting member 302 may be engaged by a plurality of bone anchors 4. In the illustrated embodiment of the invention, the connecting member 302 is engaged by four bone anchors 4. Two of the bone anchors 4 engage the first rod portion 312, and the remaining two bone anchors 4 engage the second rod portion 314. It is noted that the transition portion 310 is located between the two inboard bone anchors 4. An elastomeric spacer 160 is located between, and abuts, the two inboard bone anchors 4, thereby protecting the transition portion 310 and reinforming, or supporting, the connecting member 302. Another spacer 160 is located between, and abuts, the two right-hand bone anchors 4, as shown in FIG. 12. This second spacer lends additional strength and rigidity to the second rod portion 314. An optional third spacer 160 may be located between the two left-hand bone anchors 2. The closures used with the outboard bone anchors 4 are gripping closures, such as point and rim closures, so as to firmly lock the connecting member 302 with respect to the bone anchors 4. The closures used with the inboard bone anchors 4 may be either gripping closures or sliding closures. As discussed above, such sliding closures allow some longitudinal sliding of the connecting member 302 with regards to the bone anchor 4.

It is to be understood that while certain forms of the present invention have been illustrated and described herein, it is not to be limited to the specific forms or arrangement of parts described and shown.

What is claimed is:
1. A method of assembling a medical implant assembly having a longitudinal connecting member cooperating with a plurality of bone attachment structures, the method comprising:
providing the longitudinal connecting member comprising:
a rigid rod portion extending from a first end to a transition portion;
a flexible cord portion joined with the rigid rod portion at the transition portion and extending from the transition portion to a second end; and
a releasable end-blocker bumper portion, the releasable end-blocker bumper portion comprising a blocker portion and a tubular extension extending from the blocker portion;
engaging the rigid rod portion with a first of the plurality of bone attachment structures;
extending the flexible cord portion through a second of the plurality of bone attachment structures; and
holding at least one outer planar side surface of the releasable end-blocker bumper portion while securing the releasable end-blocker bumper portion to the flexible cord portion.
2. The method of claim 1, wherein the releasable end-blocker bumper portion further includes a bumper portion, at least a portion of the bumper portion in slidable relation with the blocker portion.
3. The method of claim 2, further comprising extending the flexible cord portion through a bore of the bumper portion.

4. The method of claim 2, wherein the bumper portion engages the tubular extension of the releasable end-blocker bumper portion in an overlapping relationship.

5. The method of claim 2, wherein the bumper portion surrounds the tubular extension of the releasable end-blocker bumper portion.

6. The method of claim 2, wherein a planar surface of the bumper portion is positioned against the blocker portion.

7. The method of claim 1, further comprising extending the flexible cord portion through a through-bore of the releasable end-blocker bumper portion, the through-bore extending through the blocker portion and the tubular extension.

8. The method of claim 1, wherein the releasable end-blocker bumper portion is releasably secured to the flexible cord portion with a threaded fastener.

9. The method of claim 1, further comprising slidably receiving at least a portion of the tubular extension of the releasable end-blocker bumper portion into a bore of a bumper portion.

10. The method of claim 1, wherein the tubular extension defines an outer cylindrical surface.

11. The method of claim 1, further comprising releasing the blocker portion from the flexible cord portion.

12. The method of claim 1, further comprising cutting the rigid rod portion to a desired length.

13. The method of claim 1, further comprising cutting the flexible cord portion to a desired length.

14. The method of claim 1, wherein the blocker portion of the releasable end-blocker bumper portion further comprises opposite planar side surfaces that are substantially parallel with respect to each other.

15. A method of assembling a medical implant assembly having a longitudinal connecting member cooperating with a plurality of bone attachment structures, the method comprising:

providing the longitudinal connecting member comprising:

a rigid rod portion extending from a first end to a transition portion;

a flexible cord portion joined with the rigid rod portion at the transition portion and extending from the transition portion to a second end; and a releasable end-blocker bumper portion, the releasable end-blocker bumper portion comprising a blocker portion and a tubular extension extending from the blocker portion;

engaging the rigid rod portion with a first of the plurality of bone attachment structures;

extending the flexible cord portion through a second of the plurality of bone attachment structures; and holding at least one outer planar side surface of the releasable end-blocker bumper portion while tensioning the flexible cord portion.

16. The method of claim 15, wherein, the flexible cord portion is tensioned before securing the releasable end-blocker bumper portion to the flexible cord portion.

17. The method of claim 15, wherein tensioning the flexible cord portion causes a bumper portion of the releasable end-blocker bumper portion to compress.

\* \* \* \* \*